US009791107B2

(12) United States Patent
Witt et al.

(10) Patent No.: US 9,791,107 B2
(45) Date of Patent: *Oct. 17, 2017

(54) PACKET-WISE PROPORTIONING FOLLOWED BY IMMEDIATE LONGITUDINAL MIXING

(75) Inventors: Klaus Witt, Keltern (DE); Konstantin Shoykhet, Karlsruhe (DE); Hans-Georg Haertl, Karlsruhe (DE)

(73) Assignee: Agilent Technologies, Inc., Santa Clara, CA (US)

( * ) Notice: Subject to any disclaimer, the term of this patent is extended or adjusted under 35 U.S.C. 154(b) by 392 days.

This patent is subject to a terminal disclaimer.

(21) Appl. No.: 14/233,966

(22) PCT Filed: Jul. 27, 2011

(86) PCT No.: PCT/EP2011/062956
§ 371 (c)(1),
(2), (4) Date: Jan. 21, 2014

(87) PCT Pub. No.: WO2013/013717
PCT Pub. Date: Jan. 31, 2013

(65) Prior Publication Data
US 2014/0251448 A1 Sep. 11, 2014

(51) Int. Cl.
*F17D 3/01* (2006.01)
*G05D 11/13* (2006.01)
(52) U.S. Cl.
CPC ............. *F17D 3/01* (2013.01); *G05D 11/133* (2013.01); *Y10T 137/2499* (2015.04)
(58) Field of Classification Search
CPC ........................................................ F17D 3/01
(Continued)

(56) References Cited

U.S. PATENT DOCUMENTS 3,802,608 A * 4/1974 Gullett .................... G01F 11/04
222/309
4,128,476 A 12/1978 Rock
(Continued)

FOREIGN PATENT DOCUMENTS

CN 1407912 4/2003
CN 1730166 2/2006
(Continued)

OTHER PUBLICATIONS

International Preliminary Report on Patentability mailed Feb. 6, 2014 for International Patent Application No. PCT/EP2011/062956.
(Continued)

*Primary Examiner* — David Sorkin

(57) ABSTRACT

A fluid supply system (150) adapted for metering two or more fluids in controlled proportions and for supplying a resultant mixture, the fluid supply system (150) comprising a plurality of solvent supply lines (104 to 107), each fluidically connected with a fluid source (100 to 103) providing a respective fluid, a pumping unit (110) comprising a reciprocating element (115) adapted for intaking fluid supplied at an inlet of the pumping unit (110) and for supplying the pressurized fluid at an outlet of the pumping unit (110), wherein the pumping unit (110) is adapted for taking in fluids from selected solvent supply lines (104 to 107) and for supplying a pressurized mixture of the fluids at its outlet, a proportioning valve (108) interposed between the solvent supply lines (104 to 107) and the inlet of the pumping unit (110), the proportioning valve (108) adapted for modulating solvent composition by sequentially coupling selected ones of the solvent supply lines (104 to 107) with the inlet of the pumping unit (110), and a longitudinal mixing unit (152) adapted for mixing longitudinally subse-
(Continued)

quent sections of the fluids so as to modify their succession in flow direction.

15 Claims, 6 Drawing Sheets

(58) Field of Classification Search
USPC .......................................... 366/160.4, 181.5
See application file for complete search history.

(56) References Cited

U.S. PATENT DOCUMENTS

| | | | |
|---|---|---|---|
| 4,155,683 A | | 5/1979 | Mochizuki et al. |
| 4,427,298 A | * | 1/1984 | Fahy ................... B01F 15/0429 137/624.18 |
| 4,475,821 A | | 10/1984 | Koch et al. |
| 4,496,245 A | | 1/1985 | Conrad et al. |
| 4,534,659 A | * | 8/1985 | Dourdeville ............ B01F 3/088 366/338 |
| 4,595,495 A | * | 6/1986 | Yotam ..................... F04B 9/042 210/101 |
| 4,883,409 A | | 11/1989 | Strohmeier et al. |
| 4,982,597 A | | 1/1991 | Berger |
| 5,234,587 A | * | 8/1993 | Allington ............... G01N 30/34 210/101 |
| 5,637,467 A | * | 6/1997 | Meltzer ................ G01N 33/528 435/188 |
| 6,116,869 A | | 9/2000 | Couillard et al. |
| 8,511,889 B2 | * | 8/2013 | Choikhet ................ B01F 5/064 138/40 |
| 2004/0014949 A1 | | 1/2004 | Dasgupta et al. |
| 2004/0042340 A1 | | 3/2004 | Aso |
| 2005/0224403 A1 | | 10/2005 | Allington et al. |

FOREIGN PATENT DOCUMENTS

| | | |
|---|---|---|
| CN | 101476222 | 7/2009 |
| CN | 102117080 | 7/2011 |
| DE | 102006058026 | 6/2008 |
| EP | 0309596 | 4/1989 |
| EP | 01174179 A1 | 1/2002 |
| EP | 1174179 | 2/2004 |
| EP | 1577012 | 9/2005 |
| GB | 2156445 | 10/1985 |
| JP | 01104989 | 4/1989 |
| JP | 2001-104989 A | 4/2001 |
| JP | 2004-508550 A | 3/2004 |
| JP | 2004508550 | 3/2004 |
| WO | WO0221121 | 3/2002 |
| WO | WO2010030720 | 3/2010 |
| WO | 2011037530 A1 | 3/2011 |
| WO | WO2011037530 | 3/2011 |

OTHER PUBLICATIONS

Office Action mailed Apr. 28, 2015 for Japanese Patent Application No. 2014-521959 (Unofficial/Non-certified translation provided by foreign agent included).
Japanese Office action dated Jan. 7, 2016 from related Japanese Patent Application No. 2014-521959.
International Search Report and Written Opinion mailed Jan. 30, 2013 for International Patent Application No. PCT/EP2011/062956.
Office Action mailed Aug. 11, 2015 in Chinese Patent Application No. 201180072423.9 (Unofficial/non-certified translation provided by foreign agent included).
Machine translation of CN101476222, published Jul. 8, 2009.
Machine translation of CN102117080, published Jul. 6, 2011.
Machine translation of CN1407912, published Apr. 2, 2003.
Machine translation of CN1730166, published Feb. 8, 2006.

* cited by examiner

PACKET-WISE PROPORTIONING FOLLOWED BY IMMEDIATE LONGITUDINAL MIXING

The present application is a National Stage application under 35 U.S.C. §365 of International Patent Application No. PCT/EP2011/062956 filed on Jul. 27, 2011 naming Klaus Witt, et al, as inventors. Priority is claimed from International Patent Application No. PCT/EP2011/062956. The entire disclosure of International Patent Application No, PCT/EP2011/062956 is specifically incorporated herein by reference.

BACKGROUND ART

The present invention relates to fluid supply systems, a configuration device, methods of operating a fluid supply system, and a software program or product. The present invention further relates to a sample separation system, in particular in a high performance liquid chromatography application.

In liquid chromatography, a fluidic sample and an eluent (liquid mobile phase) may be pumped through conduits and a column in which separation of sample components takes place. The column may comprise a material which is capable of separating different components of the fluidic analyte. Such a packing material, so-called stationary phase or sorbent which may comprise silica gel, may be filled into a column tube which may be connected to other elements (like a control unit, containers including sample and/or buffers) by conduits. The composition of the mobile phase can be adjusted by composing the mobile phase from different fluidic components with variable contributions.

EP 1,174,179 discloses a mixing apparatus where a fluid is progressing from an inlet tubing to an outlet tubing. Every segment of the liquid is part by part transferred to the outlet channel via numerous restrictor channels. The distances between the restrictor channels determine a dispersion pattern for any segment of the flow, progressing from the inlet chamber in the form of a reservoir channel to the outlet. The nearer the outlet channels are placed one to another, the higher is the permeability to the outlet collector at the respective location. Delaying partial flows of the fluid with different flow delays and providing different flow volumes for the partial flows results in a predetermined flow distribution function thus determining a dispersion pattern.

U.S. Pat. No. 4,496,245 discloses a combined proportioning valve and mixer usable in a liquid chromatography system for mixing solvents in predetermined ratios, and includes a magnetically driven stirrer rotatably disposed in a central chamber. Plural inlet lines allow solvents to enter the chamber at spaced positions. The chamber also communicates with outlet lines and is provided with means for preventing air bubbles from being entrapped in the stirrer and blocking flow through the system. Selectively controlled valve members control the flow of solvents through the inlet lines so as to achieve the preselected ratio of solvent mixing.

U.S. Pat. No. 4,155,683 discloses a system for and a method of providing an eluent composed of two different kinds of liquids being mixed at a set concentration and further a time varying concentration or mixing ratio, comprising a step for transferring each of the two liquids by sucking under low-pulsation to on-off valves, a step for periodically controlling the operation of the on-off valves, a step for controlling the amount of each liquid supplied to the mixing region during each period of valve operation, a step for substantially sucking the eluent formed by the above steps in the mixing region for discharging or supplying the same under the same low-pulsation.

U.S. Pat. No. 6,116,869 discloses a pumping system which mixes liquids with a well-controlled proportioning and flow rate. The pumping system comprises a liquid mixing device placed upstream from a pump. The liquids are taken from vessels, cyclically introduced, in a determined proportion, in a mixing chamber through alternate opening of on-off solenoid valves. The system is controlled at the input by using a damping means such as bellows in antechambers in order to avoid the effects of velocity discontinuities at the time of the opening and of the closing of the valves. The delivery of pump is controlled at the input as well as at the discharge end. The system may be used for liquid chromatography plants.

WO 2010/030720 discloses a method of reducing liquid composition errors in a low-pressure mixing pump system. Packets representing the switching intervals of each component of the desired fluid mixture are provided to an intake of the mixing pump system. For each packet, a switching time associated with at least one of the components in the packet is modulated. Modulated switching times are based on time offsets that are specifically selected according to the undesirable frequency characteristic of an intake response of the mixing pump system. The average of the volumes contributed by the packets thus modulated is equal to a component volume that achieves a desired proportion of the component in the output flow of the mixing pump system. Modulated switching times enable the reduction or elimination of composition error in the output flow of the mixing pump system.

US 2005/0224403 discloses a chromatographic monitor which includes an array of flow cells with individual light sensors that are collectively an array of photodiodes. The output from the photodiodes are multiplexed. To prevent losing information, the photodiodes are each connected to a different one of a plurality of inputs to the multiplexer through a corresponding one of a plurality of circuits that stores energy during the time the one inlet is not connected through the multiplexer to the signal processing circuitry that forms a part of an absorbance monitor.

U.S. Pat. No. 4,475,821 discloses a mixing chamber for liquids, which are supplied to the mixing chamber in measured quantities one after the other alternating over a period of time, in particular for liquid chromatographs, which is divided by a fine-pored filter plate into two areas. The inlet pipe is connected to one area and the outlet pipe is connected to the other of these areas. The two areas each widen out in a conical shape from the opening of the connected pipe towards the filter plate. The filter plate preferably consists of a steel or glass frit with a pore size in the range of 2 to 50 µm.

US 2004/042340 discloses three metal plate materials, each having penetration holes, which are united together in this order as a set at such positions that penetration holes can penetrate through the three metal plate materials so as to form a mixing portion. A plurality of sets, each having the mixing portion are integrated together at such positions that all of the penetration holes can penetrate through the respective sets of plate materials. The mixing portions of the respective sets are connected in parallel to one another.

DE 10 2006 058 026 discloses that a high performance liquid chromatography (HPLC) unit has an eluent source for producing an eluent stream in an eluent line. An injection unit is connected to the eluent line and a pillared unit is connected to the injection unit. A detector is connected to the pillared unit. A mixing chamber and a particle filter in a common mixing chamber forming a mixing chamber unit is arranged and is connected to streaming directly and consecutively.

In conventional chromatography systems in which multiple fluids are combined to form a solvent composition, artifacts in the solvent composition may occur which have a negative impact on the chromatographic performance.

DISCLOSURE

There may be a need for supplying pressurized fluid compositions with high degree of homogeneity.

According to an exemplary embodiment of a first aspect of the invention, a fluid supply system is provided which is adapted for metering two or more fluids in defined or controlled proportions and for supplying a resultant mixture, the fluid supply system comprising a plurality of solvent supply lines, each fluidically connected with a fluid source (particularly a respective reservoir or a pipeline) providing a respective fluid, a pumping unit comprising a reciprocating element adapted for intaking fluid supplied at an inlet of the pumping unit and for supplying the pressurized fluid at an outlet of the pumping unit, wherein the pumping unit is adapted for taking in fluids in defined proportions from selected solvent supply lines and for supplying a pressurized mixture of the fluids at its outlet, a proportioning valve interposed between the solvent supply lines and the inlet of the pumping unit, the proportioning valve adapted for modulating solvent composition by sequentially coupling selected ones of the solvent supply lines with the inlet of the pumping unit in the course of the fluid intake phase of the pumping unit, and a longitudinal mixing unit adapted for mixing longitudinally subsequent sections of the fluids (especially of a type for which density and/or viscosity difference plays a role) so as to modify their succession in flow direction (hence, the longitudinal direction refers to a flow direction of the sequence of fluid packets in a conduit).

According to an exemplary embodiment of a second aspect of the invention, a fluid supply system is provided which is adapted for metering two or more fluids in controlled proportions and for supplying a resultant mixture, the fluid supply system comprising a plurality of solvent supply lines, each fluidically connected with a fluid source providing a respective fluid, a pumping unit comprising a reciprocating element adapted for intaking fluid supplied at an inlet of the pumping unit and for supplying the pressurized fluid at an outlet of the pumping unit, wherein the pumping unit is adapted for taking in fluids in defined proportions from selected solvent supply lines and for supplying a pressurized mixture of the fluids at its outlet, a proportioning valve interposed between the solvent supply lines and the inlet of the pumping unit, the proportioning valve adapted for modulating solvent composition by sequentially coupling selected ones of the solvent supply lines with the inlet of the pumping unit in the course of the fluid intake phase of the pumping unit, and a mixing unit adapted for mixing subsequent sections (such as fluid packets succeeding in flow direction, layers of fluids, or fluids flowing out of a blind hole in the fluidic path) of the fluids differing in at least one of chemical composition, specific gravity, or viscosity, and wherein the mixing unit has an interior fluid accommodation volume of not more than the number of solvent supply lines multiplied by a volume of one fluid section provided by the proportioning valve (or, the mixing unit may have an interior fluid accommodation volume of not more than a sum of the partial fluid volumes provided by each of the solvent supply lines within a continuous time interval during which the proportioning valve fluidically couples sequentially each of the solvent supply lines once to the pumping unit). In this case specific gravity is referenced to the gravity of the resulting mixture. Certain sections of the fluid may be lighter or heavier than the mean or average density of the produced mixture giving rise to floatation or sedimentation.

According to an exemplary embodiment of a third aspect of the invention, a fluid supply system is provided which is adapted for metering two or more fluids in controlled proportions and for supplying a resultant mixture, the fluid supply system comprising a plurality of solvent supply lines, each fluidically connected with a fluid source providing a respective fluid, a pumping unit comprising a reciprocating element adapted for intaking fluid supplied at an inlet of the pumping unit and for supplying the pressurized fluid at an outlet of the pumping unit, wherein the pumping unit is adapted for taking in fluids in defined proportions from selected solvent supply lines and for supplying a pressurized mixture of the fluids at its outlet, a proportioning valve interposed between the solvent supply lines and the inlet of the pumping unit, the proportioning valve adapted for modulating solvent composition by sequentially coupling selected ones of the solvent supply lines with the inlet of the pumping unit, and a mixing unit adapted for splitting the fluids supplied at an outlet of the proportioning valve or at one or a plurality of points downstream from the outlet of the proportioning valve into a plurality of fluid paths with different internal fluid flow delay characteristics and adapted for combining the fluid paths at one or a plurality of rejoining points (i.e. one or more points at which the split fluids are rejoint, and which point(s) may be arranged downstream of the splitting point) to thereby mix the fluids in a longitudinal fashion (i.e. in view of different delay times which the individual fluid portions require to pass respective ones of the fluid paths, the individual fluid portions will arrive at the combining position at different times which then results in a longitudinal mixing).

According to an exemplary embodiment of a fourth aspect of the invention, a fluid supply system adapted for metering two or more fluids in controlled proportions and for supplying a resultant mixture is provided, wherein the fluid supply system comprises a plurality of solvent supply lines, each fluidically connected with a fluid source providing a respective fluid, a pumping unit comprising a reciprocating element adapted for intaking fluid supplied at an inlet of the pumping unit and for supplying the pressurized fluid at an outlet of the pumping unit, wherein the pumping unit is adapted for taking in fluids from selected solvent supply lines and for supplying a pressurized mixture of the fluids at its outlet, a proportioning valve interposed between the solvent supply lines and the inlet of the pumping unit, the proportioning valve adapted for modulating solvent composition by sequentially coupling selected ones of the solvent supply lines with the inlet of the pumping unit, and a control unit adapted for analyzing a potential incomplete mixing of the fluids in the mixture resulting from specific gravity (or density) differences between the fluids and adapted for modifying operation of the fluid supply system to at least partially suppress fluctuations resulting from incomplete mixing.

According to yet another exemplary embodiment, a sample separation system for separating components of a sample fluid (particularly a sample liquid) in a mobile phase is provided, the sample separation system comprising a fluid supply system having the above-mentioned features, the fluid supply system being adapted to drive the fluids as the mobile phase through the sample separation system, and a separation unit, preferably a chromatographic column, adapted for separating components of the sample fluid in the mobile phase.

According to an exemplary embodiment of a fifth aspect of the invention, a configuring device is provided which is adapted for configuring a fluid supply system (or a sample separation system of the above type having such a fluid supply system) adapted for metering two or more fluids in controlled proportions and for supplying a resultant mixture, the fluid supply system comprising a plurality of solvent supply lines, each fluidically connected with a fluid source providing a respective fluid, a pumping unit comprising a reciprocating element adapted for intaking fluid supplied at an inlet of the pumping unit and for supplying the pressurized fluid at an outlet of the pumping unit, wherein the pumping unit is adapted for taking in fluids from selected solvent supply lines and for supplying a pressurized mixture of the fluids at its outlet, and a proportioning valve interposed between the solvent supply lines and the inlet of the pumping unit, the proportioning valve adapted for modulating solvent composition by sequentially coupling selected ones of the solvent supply lines with the inlet of the pumping unit, wherein the configuring device comprises a determining unit adapted for determining information indicative of an incomplete mixing of the fluids in the mixture, and a mixing enhancement unit adapted for changing a configuration of the fluid supply system to thereby enhance mixing of the fluids in the mixture.

According to another exemplary embodiment of the first aspect of the invention, a method of metering two or more fluids of different specific gravity in controlled proportions and of supplying a resultant mixture is provided, wherein the method comprises fluidically connecting a plurality of solvent supply lines with a fluid source providing a respective fluid, controlling a pumping unit comprising a reciprocating element for intaking fluid supplied at an inlet of the pumping unit and for supplying the pressurized fluid at an outlet of the pumping unit, wherein the pumping unit takes in fluids from selected solvent supply lines and supplies a pressurized mixture of the fluids at its outlet, modulating solvent composition using a proportioning valve interposed between the solvent supply lines and the inlet of the pumping unit, wherein the proportioning valve sequentially couples selected ones of the solvent supply lines with the inlet of the pumping unit, and mixing longitudinally subsequent sections of the fluids so as to modify their succession in flow direction.

According to another exemplary embodiment of the second aspect of the invention a method of metering two or more fluids in controlled proportions and of supplying a resultant mixture is provided, wherein the method comprises fluidically connecting a plurality of solvent supply lines with a fluid source providing a respective fluid, controlling a pumping unit comprising a reciprocating element for intaking fluid supplied at an inlet of the pumping unit and for supplying the pressurized fluid at an outlet of the pumping unit, wherein the pumping unit takes in fluids from selected solvent supply lines and supplies a pressurized mixture of the fluids at its outlet, modulating solvent composition using a proportioning valve interposed between the solvent supply lines and the inlet of the pumping unit, wherein the proportioning valve sequentially couples selected ones of the solvent supply lines with the inlet of the pumping unit, and mixing subsequent sections of the fluids by a mixing unit having an interior fluid accommodation volume of not more than the number of solvent supply lines multiplied by a volume of one fluid section provided by the proportioning valve.

According to another exemplary embodiment of the third aspect of the invention, a method of metering two or more fluids in controlled proportions and of supplying a resultant mixture, wherein the method comprises fluidically connecting a plurality of solvent supply lines with a fluid source providing a respective fluid, controlling a pumping unit comprising a reciprocating element for intaking fluid supplied at an inlet of the pumping unit and for supplying the pressurized fluid at an outlet of the pumping unit, wherein the pumping unit takes in fluids from selected solvent supply lines and supplies a pressurized mixture of the fluids at its outlet, modulating solvent composition using a proportioning valve interposed between the solvent supply lines and the inlet of the pumping unit, wherein the proportioning valve sequentially couples selected ones of the solvent supply lines with the inlet of the pumping unit, and mixing the fluids by splitting the fluids supplied at an outlet of the proportioning valve or at one or a plurality of points downstream from the outlet of the proportioning valve into a plurality of fluid paths with different internal fluid flow delay characteristics and by combining the fluid channels at one or a plurality of points downstream of the splitting point to thereby mix the fluids in a longitudinal fashion along the flow path.

According to another exemplary embodiment of the fourth aspect of the invention, a method of metering two or more fluids in controlled proportions and of supplying a resultant mixture in a fluid supply system is provided, wherein the method comprises fluidically connecting a plurality of solvent supply lines with a fluid source providing a respective fluid, controlling a pumping unit comprising a reciprocating element for intaking fluid supplied at an inlet of the pumping unit and for supplying the pressurized fluid at an outlet of the pumping unit, wherein the pumping unit takes in fluids of different specific gravity from selected solvent supply lines and supplies a pressurized mixture of the fluids at its outlet, modulating solvent composition using a proportioning valve interposed between the solvent supply lines and the inlet of the pumping unit, wherein the proportioning valve sequentially couples selected ones of the solvent supply lines with the inlet of the pumping unit, analyzing a potential incomplete mixing of the fluids in the mixture resulting from density differences between the fluids, and modifying operation of the fluid supply system to at least partially suppress the incomplete mixing or to at least reduce sedimentation or floatation.

According to another exemplary embodiment of the fifth aspect of the invention, a method of configuring a fluid supply system adapted for metering two or more fluids in controlled proportions and for supplying a resultant mixture is provided, the fluid supply system comprising a plurality of solvent supply lines, each fluidically connected with a fluid source providing a respective fluid, a pumping unit comprising a reciprocating element adapted for intaking fluid supplied at an inlet of the pumping unit and for supplying the pressurized fluid at an outlet of the pumping unit, wherein the pumping unit is adapted for taking in fluids from selected solvent supply lines and for supplying a pressurized mixture of the fluids at its outlet, and a proportioning valve interposed between the solvent supply lines and the inlet of the pumping unit, the proportioning valve adapted for modulating solvent composition by sequentially coupling selected ones of the solvent supply lines with the inlet of the pumping unit, wherein the method comprises determining information indicative of an incomplete mixing or even sedimentation or floatation of the fluid portions in the mixture, and changing a configuration of the fluid supply system to thereby enhance mixing of the fluids in the mixture.

According to still another exemplary embodiment of the present invention, a software program or product is provided, preferably stored on a data carrier, for controlling or executing any of the methods having the above mentioned features, when run on a data processing system such as a computer (for instance a portable computer, portable data processor or dedicated controller).

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in the context of fluid supply control. The fluid supply control scheme according to an embodiment of the invention can be performed or assisted by a computer program, i.e. by software, or by using one or more special electronic optimization circuits, i.e. in hardware, or in form of program stored in non-volatile memory in controlling hardware, that is in form of embedded software, or in hybrid form, i.e. by means of combination of any of the above components. In other words, any implementation in software, firmware (embedded software) and/or hardware (for instance by an ASIC, application specific integrated circuit) is possible.

In the context of this application, the term "fluid" may particularly denote any liquid, any gas, any mixture of liquid and gas, optionally comprising solid particles. Particularly, analytes in liquid chromatography are not necessarily liquids, but can be dissolved solids or dissolved gases.

In the context of this application, the term "mixing unit" may particularly denote a fluidic member capable of promoting interaction between fluid portions to enhance homogeneity of the fluid mixture. Mixing may be performed by various ways, for instance by at least partly changing an order of a sequence of fluid packets, and/or by generating motion, particularly turbulences, in fluids so that different portions of the fluid are brought in interaction for a more homogeneous distribution of the fluid sections.

In the context of this application, the term "longitudinal mixing unit" may particularly denote a mixing unit which is capable of performing the enhancement of the interaction of different fluid sections or the change of the order of certain fluid sections in a direction along the flow path, i.e. along the lumen of a fluidic conduit rather than only perpendicular thereto. The mixing performance of such a longitudinal mixing unit may therefore be anisotropic with the flow direction forming the preferred direction.

In the context of this application, the term "interior fluid accommodation volume" may particularly denote the volume of a hollow space within the respective mixing unit which can be filled with the fluid to be mixed. In an embodiment, the fluid packets to be mixed within one batch (such a batch including one fluid packet from each of the active solvent supply lines) may have a volume which is not smaller than the interior fluid accommodation volume. In other words, the mixer volume is not larger than a fluid volume of one batch. For instance, the proportioning valve may define, by its switching logic, the individual volumes of the fluid packets from the individual solvent supply lines. The sum of these individual volumes within one batch, as defined by the proportioning valve, may be larger than (or equal to) than the interior fluid accommodation volume of the mixing unit.

In the context of this application, the term "interior path volume" may particularly denote a volume of a hollow space (such as a lumen) within the respective flow path which can be filled with the respective fluid.

In the context of this application, the term "density differences" or "specific gravity differences" may particularly denote that individual sections of the fluids originating from the different solvent containers may have a different physical density. For instance, water and acetonitrile (ACN) or other organic solvents may differ significantly with regard to their density so that individual sections of the mixed fluid may be unintentionally separated due to the different impact of gravity or buoyancy forces.

In the context of this application, the term "sedimentation" may particularly denote that, in view of density differences (or specific gravity differences) and/or differences concerning other physical parameters such as viscosity, different sections of the fluids may be separated unintentionally, and one fraction may sediment below another one. Likewise a fraction may float in the fluid.

In terms of metering two or more fluids in controlled proportions and supplying a resultant mixture it is believed to be very disturbing, if a portion of liquid of extreme specific density gets departed from the flow stream and rests in a section from which it may be mobilized at some later time point. Such behavior will introduce a compositional variance, with a net effect of zero but occurring over an unpredictable volume of the delivered fluid. This disturbance volume may span across multiple pump strokes or even be in access of the total system volume or even the retention volume of the separated peaks. So the natural system dispersion by no means has a chance to suppress this disturbance.

In the context of this application, the term "internal fluid flow delay characteristics" may particularly denote that in the different fluidic channels forming the flow path, at least one flow-related parameter may differ so that the delay which a fluid experiences when passing through this flow channel is different for the different flow paths. For instance, if a path length or an internal volume of the respective paths differs among the different paths, a fluid which has to flow along a longer conduit or a larger volume may be delayed stronger than another fluid which flows along a short or low volume path. Also the flow impedance (which may depend on a geometry, surface finish or temperature of flow path conduits) acting on the fluid when flowing through the respective flow paths may have an impact on the delay. By adjusting a different delay for the different fluid portions, proper mixture may be promoted as later portions may overtake earlier ones.

In the context of this application, the term "changing a configuration of the fluid supply system to thereby enhance mixing" may particularly denote that the fluid supply system is manipulated in such a manner that an improper or insufficient mixing or a controversial sedimentation or floatation is at least partially compensated for or reduced respectively and the various fluids are mixed or redistributed more efficiently. For instance, a system configuration may be changed in response to an analysis of the impact of density fluctuations along a fluidic path. A change of a configuration (for instance of an operation of the mixing unit) may then be performed so as to improve the mixing.

Exemplary embodiments of the invention are based on a detailed analysis of a shortcoming of conventional fluid supply systems, particularly for fluid separation systems like chromatographic devices. Conventionally, artifacts which may occur in such systems have been interpreted erroneously by the skilled persons, and the present inventors have now succeeded in properly understanding the origin of such artifacts. In a scenario in which sequential fluid packets, as different solvent compositions, are introduced into a fluidic path to be mixed for use as a solvent for a sample separation procedure, improperly mixed portions in the fluid column have been detected experimentally in the form of composition disturbances or irregularities or peaks of certain solvent components. It has also been observed by the present inventors that such artifacts occur, in certain instances, periodically or quasi-periodically with a repetition time which may be very long as compared to a time slice assigned to a volume of one stroke of the pumping unit. Artifacts with a repetition distance as large as, for instance, 20 to 60 strokes have not previously been understood by the skilled persons. The present inventors have now systematically discovered that the origin of such artifacts is an improper mixing of fluid components of a mixture which have strongly varying density and/or viscosity. The inventors have identified layering effects or stratification of sections of relatively high and relatively low density in a flow path, for instance when mixing water and acetonitrile (ACN) as used frequently for HPLC applications. It has further been identified by the inventors that also different viscosity values of different fluid components may result in a poor mixing of such components, which in turn results in stimulation or amplification of the—artifacts described above.

Although many effects may contribute to the undesired layer-wise distribution of the individual fluid components resulting in a random or quasi-periodic pattern of artifacts, the present inventors have further discovered in accordance with embodiments of a first aspect of the invention that an intense suppression of artifacts can be achieved by promoting mixing of the fluids in the longitudinal direction of the fluid flow. Such a longitudinal mixing may be performed to redistribute the parts of individual fluid packets, for instance by forcing parts of a certain fluid packet having a certain density and viscosity to overtake parts of another fluid packet having another density and/or viscosity so that individual fluid sections differing in their density become smaller in volume and distributed closer to one another, so that axial mixing can become efficient in suppression of stratification.

In accordance with embodiments of a second aspect of the invention, it has been discovered that the use of a mixing unit with a very small internal volume (particularly a fluid accommodation volume of the mixing unit being not larger than the fluid volume displaced during one stroke of the pumping unit) can very efficiently improve the mixture homogeneity in the system. By providing a mixing unit with a small internal volume, an undesired formation of a mixture with historic fluid in the path may be prevented, improving speed of e.g. gradient analysis. The longitudinal mixing in this case is not primarily meant to mix across multiple intake strokes, but rather to prevent sedimentation or floatation of individual fluid portions, which, if occurs can give rise to sporadic or quasi-periodic disturbances with characteristic intervals very much longer, than the duration of a single pump cycle (stroke).

In accordance with embodiments of a third aspect of the invention, it has been discovered that splitting the fluid packets into hydraulically parallel channels with designed transition time values for a respective fluid packet and by combining the fluid packets again after they have passed the respective channel also has a highly advantageous impact on the suppression of artifacts.

In accordance with embodiments of a fourth aspect of the invention, it has been discovered that a sequence of identifying improperly mixed sections in the fluid mixture, changing a machine-related parameter, and monitoring whether such change reduced the artifacts, can be used for systematic suppression of the artifact formation. For instance, also parameters such as a length, an orientation and a tilt of a conduit connecting different components of the fluid supply system may have a significant impact on the artifacts and may be changed for promoting homogeneity of the supplied mixture.

In accordance with embodiments of a fifth aspect of the invention, it is also possible that during a calibration or configuration procedure the fluid supply system is analyzed with regard to mixing artifacts caused by to density fluctuations. During such a procedure, the occurrence of stratification effects, etc. may be detected, and the efficiency and accuracy of the fluid supply can be improved by taking countermeasures in order to improve mixing.

In the following, further exemplary embodiments of the fluid supply systems will be explained. However, these embodiments also apply to the sample separation system, the configuration device, the methods, and the software program or product.

In an embodiment, the different internal fluid flow delay characteristics are provided by different internal fluid path volumes. If the fluid is split into different fluid path volumes, the delay time for passing through the volumes differs so that, when the fluids are reunified at the end of the splitting path, individual sections are split and distributed in space, so improved mixing occurs.

In an embodiment, the different internal fluid flow delay characteristics are provided by different internal fluid path flow resistances. In such a scenario, the flow resistance is used as a design parameter in order to adjust different delay times for the fluid portions passing through the flow paths. For instance, even if the volume of different flow paths is the same but the flow paths differ concerning diameter and length of the fluid conduits, a long and narrow fluidic path will provide more friction than a short and large diameter flow path which will result in different flow resistance values and hence different traversing/transport times of the fluids through the various flow paths.

In an embodiment, the mixing unit is located downstream of the proportioning valve and upstream of the pumping unit. Arranging such a kind of mixture structure on the low pressure side of the pumping unit has turned out to be particularly efficient for promoting homogeneity of the mixture. It is found that the origin of improper mixing occurs particularly close to the proportioning valve and since operation of the pumping unit shall be preferably done with an already properly mixed fluid composition, locating the mixing unit between proportioning valve and pumping unit is particularly appropriate.

In an embodiment, the mixing unit is adapted for at least partially equilibrating density gradients across subsequent sections of the fluids, preventing sedimentation/floatation. Thus, the mixing unit may be controlled or may be configured so that differences concerning specific gravity of different fluid packets along a flow path are at least partially compensated for by the performance of the mixing unit. In other words, the equilibration of density fluctuations may be used as a static design parameter or as a dynamic control parameter for the mixing unit.

In an embodiment, a flow path downstream of the outlet of the proportioning valve is configured to prevent modification of the distribution of the fluids caused by differences in their specific gravity. More specifically, a flow path downstream of the outlet of the proportioning valve may be configured to prevent modification of the distribution of the fluids within subsequent sections of the fluids caused by differences in their specific gravity, and the mixing unit may be adapted for at least partially equilibrating density fluctuations in subsequent sections of the fluids. Therefore, this flow path may be specifically configured to inhibit layering effects which may result from different density values.

In an embodiment, the mixing unit has an interior fluid accommodation volume of not more than about 100 µl, particularly of not more than about 50 µl, more particularly of not more than about 10 µl. With such small interior fluid accommodation volumes, proper mixing of very small numbers of packets may be initiated.

In an embodiment, the mixing unit comprises or consists of a knotted tubing, particularly a knotted intake tubing arranged in a flow path between the proportioning valve and the pumping unit. Knotting a flexible tubing has turned out as a simple but very efficient measure of intentionally disturbing the flow and initiating an effective mixing. Knotting a tubing for artifact suppression may be particularly efficient in a conduit between proportioning valve and pumping unit.

In an embodiment, the mixing unit comprises or consists of a tubing having an inner lumen (for instance having a circular cross-section) which has one or more mixing structures (as intentional flow disturbance structures) each providing a respective contribution to a flow resistance of the fluids in the lumen. For instance, a cylindrical lumen may be equipped with one or more lateral extensions disturbing the flow and improving a mixing performance. For instance, such mixing structures may comprise a comb structure, a vein structure, a multi-lumen tubing, a foam insert, one or more nozzles, a vortex, one or more pillars, a side volume having a rectangular cross-section, a plurality of side volumes having a rectangular cross-section with different volume values, a plurality of side volumes extending from the lumen along different directions, a side volume having a polygonal cross-section with an angle differing from a right angle, a zig-zag portion of the lumen, etc. Of course, other kind of mixing structures may be implemented as well.

In an embodiment, the mixing unit comprises an inlet configured for receiving the fluids as an inlet flow, an outlet configured for providing the mixed fluids an outlet flow, and a plurality of flow channels coupled between the inlet and the outlet, a flow distributor for distributing the inlet flow into the plurality of flow channels so that each flow channel receives a partial flow from the inlet flow, and a flow combiner for combining the partial flows from the plurality of flow channels to the outlet flow, wherein each flow channel comprises a first flow section having a hydraulic resistance substantially representing a significant hydraulic resistance of the flow channel, one or more of the flow channels each comprise a second flow section coupled in series with the first flow section of the respective flow channel, each second flow section comprises a volume that is flown through by the fluid and delays fluid propagation from the first flow section to the flow combiner by a time required by the respective partial flow to pass the volume of the respective second flow section, and the distribution of the partial flows into the flow channels is substantially independent of the viscosity of the fluid. As the distribution of the partial flows in such embodiments is substantially independent of the viscosity of the fluid, the mixer shows an improved characteristic in particular in such applications wherein the viscosity of the fluid varies over time. In HPLC, a typical application with varying viscosity is the so-called gradient mode, wherein the composition of the fluid is varied over time by changing the mixing ratio for a plurality of different solvents over time. As an example, two solvents water and acetonitrile (ACN; formula: $CH_3CN$) might be mixed for providing the mobile phase. In gradient mode, the mixing ratio between water and acetonitrile is varied (e.g. continuously or stepwise) over time, e.g. starting from hundred percent water to hundred percent acetonitrile. Viscosity of the mixed fluid (here the mobile phase) depends on the actual mixing ratio and thus becomes a function over time during gradient mode. With the independency of the distribution of the partial flows onto the viscosity of the fluid, the mixing of the fluid as provided by the mixer also becomes substantially independent on the viscosity of the fluid, so that the mixer becomes in particular suitable and advantageous for applications wherein the viscosity of the fluid varies over time, such as in the aforementioned gradient mode in HPLC. Also, composition change of the eluent with this mixer embodiment takes place in a predictable and reproducible manner nearly independently on the special properties of the solvents.

In an embodiment, the mixing unit comprises an inlet configured for receiving the fluids as an inlet flow, an outlet configured for providing the mixed fluids as an outlet flow, and a plurality of flow channels coupled between the inlet and the outlet, a flow distributor for distributing the inlet flow into the plurality of flow channels so that each flow channel receives a partial flow from the inlet flow, and a flow combiner for combining the partial flows from the plurality of flow channels to the outlet flow, wherein each flow path comprises a flow direction change forcing the fluid to flow at varying angles with respect to a direction of gravitational in the consequent sub-sections of the flow path. Such a flow direction change has turned out to efficiently enhance mixing.

In an embodiment, during an intake movement of the reciprocating element, when fluid is drawn in via the inlet of the pumping unit, the proportioning valve performs switching between different solvent supply lines. Therefore, fluid mixing can be performed by switching during the intaking process. It is also possible that, between intervals during which the fluid is drawn in via the inlet of the pumping unit, the proportioning valve performs switching between different solvent supply lines. Hence, the switching may even be performed in time intervals during which the fluid rests.

In an embodiment, the proportioning valve has a plurality of switching valves, with the switching valves being sequentially actuated during an intake movement of the reciprocating element of the pumping unit. Each of the switching valves may be formed by two switching members, i.e. a stator and a rotor, being rotatable relative to one another for switching.

In an embodiment, the proportioning valve is configured for selecting a selected one of the solvent supply lines corresponding to a multiplexer scheme. In this context, the term "multiplexer" may denote that, at a time, always one of multiple switching valves is coupled to the pumping unit. A multiplexer selects one of several input fluid flows and forwards the selected input fluid flow into a single output fluid flow. It is particularly possible to connect two valves in parallel with two sources of the same solvent and to switch the valves simultaneously or in an overlapping manner. This may be advantageous since the flow through two valves may have desirable properties so that it may be appropriate to allow the two valves to be opened at the same time.

In an embodiment, predefined portions of an intake movement of the reciprocating element are assigned to different solvents that are drawn in into the pumping unit, wherein proportioning is done by metering of one of volumetric packets, time slices, and position of the reciprocating element. In this context, a volumetric packet may define a fluid portion having a defined volume. The term "time slices" may denote a certain defined time intervals which define a single phase within a reciprocating element's duty cycle which then, given a defined motion pattern of the reciprocating element, translates into a defined intake volume portion. The position of the reciprocating element in a pumping chamber at the beginning of an intake process as compared to a reference position (for instance a reverse point in a pumping chamber) may also be used as a measure for a fluid amount to be metered.

In an embodiment, the control unit is adapted for at least partially suppressing the sedimentation/floatation due to incomplete mixing by adjusting a stroke of the reciprocating element, adjusting a size of fluid packets provided by the proportioning valve, adjusting an intake velocity of the fluids by the pumping unit, adjusting an order at which the pumping unit intakes the fluids, overlaying a dither to a control system for controlling at least one of the proportioning valve and the pumping unit, rapidly transferring a content a pumping chamber of the pumping unit into other parts of the fluid system, adjusting a solvent composition, and/or adding an additive to the fluids promoting mixture. In other embodiments, the control unit may change other parameters of the system so as to improve mixing of the fluids.

In an embodiment, the pumping unit comprising a further reciprocating element adapted for displacing, in cooperation with the reciprocating element, the fluid supplied at the inlet of the pumping unit and for supplying the fluid further pressurized at the outlet of the pumping unit. In this embodiment, more than one reciprocating element, for instance two pistons, may reciprocate in one and the same pumping chamber. The multiple reciprocating elements may all be controlled as described above for the case of a single reciprocating element only.

In an embodiment, the fluid supply system comprises a further pumping unit arranged downstream of the pumping unit and adapted for displacing, by a further reciprocating element, the fluid supplied at the outlet of the pumping unit and at an inlet of the further pumping unit and for supplying the fluid further pressurized at an outlet of the further pumping unit. In this embodiment, several pumping units with individual reciprocating elements and chambers may be provided. For instance, multiple pumping units may be hydraulically coupled in series. The multiple pumping units may all be controlled as described above for the case of a single pumping unit only.

In an embodiment, the reciprocating element comprises a piston, a membrane, or may be adapted as a pressure chamber. However, other embodiments of the reciprocating element are possible as well as long as the reciprocating element is capable of reciprocating within the pumping chamber resulting in reciprocating changes of the volume available to fluid within chamber.

In the following, further exemplary embodiments of the configuration device will be explained. However, these embodiments also apply to the sample separation system, the fluid supply systems, the methods, and the software program or product.

In an embodiment, the determining unit is adapted for analyzing artifacts in terms of a sample separation performed using the incompletely mixed fluid mixture. The mixing enhancement unit may then be adapted for changing a configuration of the fluid supply system to thereby enhance sample separation performance. In such an embodiment, the undesired effects of improper mixing of solvent component may be detected indirectly by its impact on the chromatographic separation performance. This information may then be specifically processed by the mixing enhancement unit for improving mixture.

In an embodiment, the determining unit is adapted for determining information indicative of layer formation between fluids having different density and/or different viscosity. For example, it is possible to model layer formation by considering the acting forces (such as the gravity force) and/or interaction between fluidic portions.

In an embodiment, the determining unit is adapted for identifying at least one historic fluid section in the mixture getting stuck or moving backwards in the flow path between the solvent supply lines and the pumping unit. The mixing enhancement unit may then be adapted for forcing the historic fluid section forwardly in the flow path. Historic fluid sections, i.e. fluid sections remaining in conduits or fluidic members of the fluid supply system significantly longer than normal or desired, and which for instance may be trapped in specific sections of the fluidic parts in view of their respective specifically large or small density values, have been identified by the present inventors as an origin of artifacts. Configuring the flow path or operation of the fluid supply system so that the generation of pockets filled with historic fluid sections can be prevented allows to further improve the provision of property mixed fluids.

In an embodiment, the determining unit is adapted for localizing a position in the flow path at which incomplete mixing of the fluids in the mixture occurs. The mixing enhancement unit may then be adapted for changing the configuration of the fluid supply system (specifically at the detected location or locations) to thereby enhance mixing of the fluids at the localized position. This can be for instance performed by one or more sensors arranged at certain positions which allow for identifying improperly mixed portions of the fluid. For example, fluorescence measurements or the like may be performed along the flow path at certain positions allowing for estimating positions at which the various fluids are not mixed properly.

In an embodiment, the mixing enhancement unit is adapted for controlling a mixing unit of the fluid supply system for mixing subsequent sections of the fluids to thereby enhance mixing of the fluids in the mixture. For example, the mixing unit may have one or more adjustable parameters having an impact on the characteristics of the mixture of the fluidic components.

In an embodiment, the mixing enhancement unit is adapted for changing the configuration of the fluid supply system by changing at least one parameter value of a set of parameters defining an operation mode of the fluid supply system, changing at least one fluid of the fluid supply system, changing at least one component of the fluid supply system, and/or changing at least one geometrical condition of fluid supply system. Such parameters may be changed in correspondence with the desired mixing properties.

In an embodiment, the determining unit is adapted for determining information indicative of an incomplete mixing of the fluids in the mixture at a specific flow path position in the fluid supply unit. The inventors have identified a conduit between the proportioning valve and the pumping unit, and a pumping chamber of the pumping unit as flow path positions specifically prone to facilitate such stratification or undesired redistribution of the fluids. A connection capillary between proportioning valve and pumping unit has been specifically identified as a critical section along the fluidic path at which artifacts may be generated. Also the volume with the pumping chamber is prone to layer formation by individual portions of the fluid.

In an embodiment, the mixing enhancement unit is adapted for controlling the pumping unit so that the reciprocating element is positioned at a lower reversal point within a pumping chamber when the fluid having the largest density among the fluids supplied by the fluid supply conduits is located at a bottom section of the pumping chamber. Controlling the piston to be at its lowermost position when the fluid with the largest density is located at a bottom section of the pumping chamber may efficiently prevent this fluid from causing artifacts.

In the following, further exemplary embodiments of the sample separation system will be explained. However, these embodiments also apply to the fluid supply systems, the configuration device, the methods, and the software program or product.

According to embodiments of the present invention, the sample separation system further comprises at least one of: a sample injector adapted to introduce the sample into the mobile phase; a detector adapted to detect separated components of the sample; a collection unit adapted to collect separated components of the sample; a data processing unit adapted to process data received from the liquid separation system; a degassing apparatus for degassing the mobile phases; a separating unit such as a chromatographic column for separation of the sample components.

Embodiments of the present invention might be embodied based on most conventionally available HPLC systems, such as the Agilent 1290 Series Infinity system, Agilent 1200 Series Rapid Resolution LC system, or the Agilent 1100 HPLC series (all provided by the applicant Agilent Technologies—see www.agilent.com—which shall be incorporated herein by reference).

One embodiment of an HPLC system comprises a pumping apparatus having a piston for reciprocation in a pump working chamber to compress liquid in the pump working chamber to a high pressure at which compressibility of the liquid becomes noticeable, and to deliver said liquid at high pressure.

One embodiment of an HPLC system comprises two pumping apparatuses coupled either in a serial or parallel manner. In the serial manner, as disclosed in EP 309596 A1, an outlet of the first pumping apparatus is coupled to an inlet of the second pumping apparatus, and an outlet of the second pumping apparatus provides an outlet of the pump. In the parallel manner, an inlet of the first pumping apparatus is coupled to an inlet of the second pumping apparatus, and an outlet of the first pumping apparatus is coupled to an outlet of the second pumping apparatus, thus providing an outlet of the pump. In either case, a liquid outlet of the first pumping apparatus is phase shifted, preferably essentially 180 degrees, with respect to a liquid outlet of the second pumping apparatus, so that only one pumping apparatus is supplying into the system while the other is intaking liquid (e.g. from the supply), thus allowing to provide a continuous flow at the output. However, it is clear that also both pumping apparatuses might be operated in parallel (i.e. concurrently), at least during certain transitional phases e.g. to provide a smooth(er) transition of the pumping cycles between the pumping apparatuses. The phase shifting might be varied in order to compensate pulsation in the flow of liquid as resulting from the compressibility of the liquid. It is also known to use three piston pumps having about 120 degrees phase shift.

The separating device preferably comprises a chromatographic column providing the stationary phase. The column might be a glass or steel tube (e.g. with a diameter from 10 μm to 10 mm and a length of 1 cm to 1 m) or a microfluidic column (as disclosed e.g. in EP 1577012 A1 or the Agilent 1200 Series HPLC-Chip/MS System provided by the applicant Agilent Technologies, see e.g.www.chem.agilent.com). The individual components are retained by the stationary phase differently and separate from each other while they are propagating at different speeds through the column with the eluent. At the end of the column they elute separated, more or less one at a time. During the entire chromatographic process or during certain phases thereof the eluent might be also collected in a series of fractions. The stationary phase or adsorbent in column chromatography usually is a solid material. The most common stationary phase for column chromatography is surface modified silica gel, followed by silica gel and alumina. Cellulose powder has often been used in the past. Known are ion exchange chromatography, reversed-phase chromatography (RP), normal phase chromatography, hydrophilic interaction chromatography, size exclusion chromatography, affinity chromatography etc. The stationary phases are usually fine powders or gels whereas the particles can be partially or entirely meso- and or microporous providing extended surface area. Furthermore, there also exist monolithic columns comprising continuous porous stationary phase body for fast high performance liquid chromatography separations.

The mobile phase (or eluent) can be either a pure solvent or a mixture of different solvents. It can be chosen e.g. to adjust the retention of the components of interest and/or to minimize the amount of mobile phase to run the chromatography. The mobile phase can preferably be chosen so that the different components can be separated and/or isolated effectively. The mobile phase might comprise an organic solvent like e.g. methanol or acetonitrile, preferably diluted with water. For gradient operation water and organic solvent may be delivered from separate supply lines or reservoirs, from which the gradient pump delivers a programmed blend to the system. Other commonly used solvents may be isopropanol, tetrahydrofuran (THF), hexane, ethanol or other organic or inorganic liquid components and/or any combination thereof or any combination of these with aforementioned solvents or premixed mixtures comprising any of the aforementioned solvents including water.

The sample liquid might comprise any type of process liquid, natural sample like juice, body liquids like plasma or it may be the result of a reaction like from a fermentation broth.

The fluid is preferably a liquid but may also be or comprise a gas and/or a supercritical fluid (as e.g. used in supercritical fluid chromatography—SFC—as disclosed e.g. in U.S. Pat. No. 4,982,597 A).

The pressure in the mobile phase might range from 2-200 MPa (20 to 2000 bar), in particular 10-150 MPa (100 to 1500 bar), and more particularly 50-120 MPa (500 to 1200 bar).

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in or by the control unit.

BRIEF DESCRIPTION OF DRAWINGS

Other objects and many of the attendant advantages of embodiments of the present invention will be readily appreciated and become better understood by reference to the following more detailed description of embodiments in connection with the accompanying drawings. Features that are substantially or functionally equal or similar will be referred to by the same reference signs. The illustration in the drawing is schematic.

Figure 1:
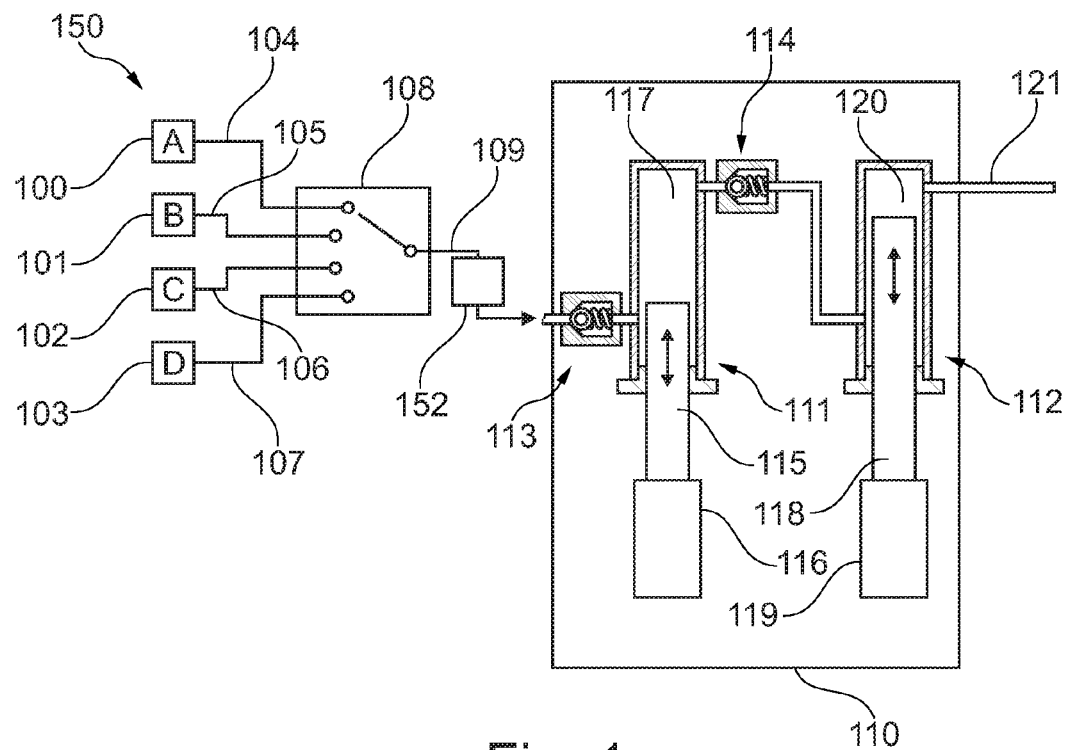
FIG. 1 illustrates a fluid supply system according to an exemplary embodiment of the invention.

The illustration in the drawing is schematic.

In an embodiment, a low-pressure mixing technology is provided addressing density effects like sedimentation by a packet-wise proportioning followed by immediate longitudinal mixing.

In high-performance liquid chromatography (HPLC) systems usually the more cost efficient implementations are based on a low-pressure solvent proportioning during the intake phase, followed by a pump that produces a high pressure. Because of the related economic advantage, often a 4-channel proportioning valve is used, which is a characteristic part of a so called "quaternary system". Although quaternary systems are cheap and flexible because of their gradient capabilities across up to four different solvent constituents, still in terms of performance they rank behind binary pumping performance. One of the shortcomings of such conventional systems is in terms of gradient delay, while the other is in terms of gradient precision. While gradient precision, defined in general as compositional stability of the mixture generated by the pump, can be improved by adding mixing volume downstream of the pump, this however increases the shortcoming in terms of gradient delay significantly.

It has now been discovered that regular and irregular fluctuations of the composition of the solvent mixture can be caused by conditions allowing for solvent layering or stratification in the parts of the system downstream of a proportioning valve, more specifically downstream of a 4-channel proportioning valve, (further on referred generally to as a multi-channel proportioning valve or a multi-channel gradient valve, MCGV). Further on it was discovered that these fluctuations can be substantially reduced with limited amount of mixing volume placed upstream to the pump, while adding little mixing downstream from the pump will not help a lot (which is unexpected for a person skilled in the field of liquid chromatography).

Real-life measurements in the lab show that significant compositional disturbances often spread across a long series of strokes (easily a set of 50 strokes). Still such disturbances can show up in a regular pattern (stable frequency). So it is believed that there is an element in the system, which can keep a track of the history for longer than the transport time of the entire liquid volume of the system. E.g. while the system volume is roughly 1 ml, these disturbances may show up, pretty repeatably, 2.5 ml apart. Such artifacts have not been understood for a long time.

The present inventors have now found in a very long series of elaborate tests that this effect relates to the solvent types being used. When mixing liquids, which are significantly different in density, the pattern representing the aforementioned composition disturbances is more pronounced. Additionally, a strong dependence of this pattern on the stroke volume setting can be observed.

In such a low-pressure proportioning regime it may happen that at the end of the intake stroke actually the liquid portion that is located at the inlet valve (bottom of the primary cylinder) is either water or acetonitrile.

In the case acetonitrile is a liquid filling the inlet portion of the pump cylinder during the primary deliver stroke cycle, the acetonitrile yet not completely mixed with the content of the pump cylinder may float in the liquid mixture in the pump head. This floating liquid plug now may accumulate, eventually at the piston seal recess, which is one of the topmost parts in the pump chamber.

Whenever an accumulated amount of floating liquid is enough and the flowing stream will have a chance to mobilize at least a portion of it, then an unexpected, uncontrolled and undesired plug of higher organic composition will be moved through the system.

The same effect may occur in the inlet tube, which connects from a multi channel gradient valve to the inlet valve of the pumping unit as well as in any part of the flow path where density-driven separation of liquids is possible. E.g. water can sediment at the lowest point of this tube. Often it is possible to generate a dip in the organic content trace by just ticking on the inlet tube (disturbing the otherwise relatively calm plug of higher density solvent).

In view of this discovery, the present inventors propose countermeasures to suppress corresponding artifacts.

One countermeasure relates to an intensive mixing of packet-wise proportioned solvent plugs (without wasting too much of volume) yielding proper results.

Another countermeasure relates to minimizing or preventing any volume, in which historic solvent (floating or sedimenting) may be stored and eventually (sporadic event) bleeds back into the flow stream. Special inserts or geometries can be added to support homogeneous flushing.

FIG. 1 shows a liquid supply system adapted for metering liquids in controlled proportions and for supplying a resultant mixture. The liquid supply system comprises four reservoirs 100, 101, 102, 103, with each of the reservoirs containing a respective solvent, A, B, C, D. Each of the reservoirs 100 to 103 is fluidically connected via a respective liquid supply line 104, 105, 106, 107 with a proportioning valve 108. The proportioning valve 108 is adapted to connect a selected one of the four liquid supply lines 104 to 107 with a supply line 109, and to switch between different liquid supply lines. The supply line 109 is connected with an inlet of a pumping unit 110. Hence, solvent metering is performed at the low-pressure side of the pumping unit 110.

In the example shown in FIG. 1, the pumping unit 110 comprises a first piston pump 111 fluidically connected in series with a second piston pump 112. The first piston pump 111 is equipped with an inlet valve 113 and with an outlet valve 114. A first piston 115 is driven by a first motor 116 and reciprocates within the first pump chamber 117. A second piston 118 is driven by a second motor 119 and reciprocates within a second pump chamber 120. Alternatively, both pistons 115, 118 can be operated by a common drive system, e.g. a differential drive or gear.

During an intake phase of the first piston pump 111, the inlet valve 113 is open, the outlet valve 114 is closed, and the first piston 115 moves in the downward direction. Accordingly, solvent supplied via the supply line 109 is drawn into the first pump chamber 117. During the downward stroke of the first piston 115, the proportioning valve 108 may switch between different liquid supply lines and hence between different solvents. Thus, during the downward stroke of the first piston 115, different solvents may be drawn into the first pump chamber 117 one after the other. In an alternative construction, there may be individual inlet valves for each liquid supply line 104 to 107, which then are controlled like and instead of proportioning valve 108.

In a flow path between the proportioning valve 108 and the pumping unit 110, a mixing unit 152 is interconnected. The mixing unit 152 is provided for mixing the various fluid packets supplied at an outlet of the proportioning valve 108 and being potentially improperly mixed. In different embodiments of the invention, the mixing unit 152 may be configured in a different way so as to achieve improved mixing and finally suppression of artifacts at conduit 121 which artifacts arise from the composition disturbances upstream of the conduit 121, especially from the liquid distribution irregularities in the supply line 109 or cylinder chamber 117 as described above. In one embodiment, the mixing unit 152 is configured as a longitudinal mixing unit for mixing longitudinally subsequent sections of the fluid so as to modify their succession in flow direction. Hence, when portions or parts of a fluid packet in a sequence of fluid packets are differently delayed they get distributed over other fluid packets, and thus the packets will automatically be mixed by distributing their parts along the succession of the packets. This redistribution of parts of the packets automatically brings these fluid packets in interaction and therefore promotes effective mixture in a longitudinal direction, i.e. along a flow path.

It is also possible that the mixing unit 152 of FIG. 1 is specifically adapted for mixing subsequent sections of the fluids and has an interior fluid accommodation volume of not more than the number of solvent supply lines 104 to 107 (i.e. four) multiplied by a volume of one fluid section provided by the proportioning valve 108. In the shown embodiment, there are four solvent supply lines 104 to 107. The volume of one section can be taken from FIG. 2, since the time slices during which one of the fluid containers 100 to 103 is connected to the conduit 109 also (in combination with a flow velocity) define a volume in accordance with a used metering scheme. By correspondingly dimensioning the mixing unit 152 with a very small internal volume, basically only sufficient to accommodate a full set of fluid packets, one from each of the containers 100 to 103, can be accommodated within the mixing unit 152 at the same time, which results in improved mixing.

In still another embodiment, the mixing unit 152 of FIG. 1 is adapted for splitting the fluids supplied at an outlet of the proportioning valve 108 at one or a plurality of points downstream from the outlet of the proportioning valve 108 into a plurality of flow paths with different internal fluid flow delay characteristics. In this scenario, the mixing unit 152 may be further adapted for combining the flow paths at one or a plurality of points downstream of a splitting point to thereby mix the fluid in a longitudinal fashion. By splitting the fluid into different paths having different internal volumes and/or different flow resistance values and by later combining them after flowing through the various flow paths, the different delays relating to the various fluid paths may result in an efficient mixing and therefore suppression of composition fluctuations caused by undesired liquid redistribution driven by density differences or gradients.

Figure 2:
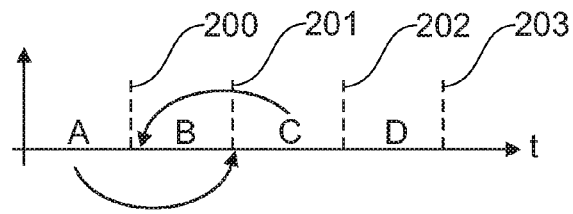
FIG. 2 schematically illustrates a sequence of fluid packets injected with the fluid supply system of FIG. 1, and illustrates that the order of the fluid packets may be changed.

FIG. 2 shows an example of three different solvents A, B, C being drawn into the first pump chamber 117 during the downward stroke of a first piston in accordance with a given metering scheme. Initially, the first liquid supply line 104 is connected to the pumping unit's inlet, and solvent A is drawn into the first pump chamber 117. After the first piston 115 has drawn in a certain amount of solvent A, the proportioning valve 108 switches from solvent A to solvent B at a point of time 200. Next, a certain amount of solvent B is drawn in via the second liquid supply line 105. At a point of time 201, the proportioning valve 108 switches from solvent B to solvent C. Then, a certain amount of solvent C is drawn into the first pump chamber 117 until a point of time 203. Then, a certain amount of solvent D is drawn into the first pump chamber 117. The point of time 203 indicates the end of the first piston's downward stroke.

During the downward stroke of the first piston 115, the second piston 118 performs an upward stroke and delivers a flow of fluid, and at the pumping unit's outlet 121, a flow of composite solvent at high pressure is provided.

After the respective amounts of different solvents have been drawn into the first pump chamber 117, the inlet valve 113 is shut, the first piston 115 starts moving in the upward direction and compresses the liquid contained in the first pump chamber 117 to system pressure. In an alternative construction, when the proportioning valve 108 is capable to withstand high pressure, an extra inlet valve 113 may be omitted. The outlet valve 114 opens, and during the following solvent transfer phase, the first piston 115 moves in the upward direction, the second piston 118 moves in the downward direction, and the composite solvent is transferred from the first pump chamber 117 to the second pump chamber 120. During the solvent transfer phase, the amount of composite solvent supplied by the first piston pump 111 exceeds the amount of composite solvent drawn in by the second piston pump 112, and hence, at the outlet 125, a continuous flow of composite solvent is maintained.

After a well-defined amount of composite solvent has been supplied from the first piston pump 111 to the second piston pump 112, the outlet valve 114 is shut, the second piston 118 moves in the upward direction, thus a continuous flow of composite solvent is maintained, while the first piston 115 starts moving in the downward direction, the inlet valve 113 is opened, and again different solvents are drawn into the first pump chamber 117.

Figure 3:
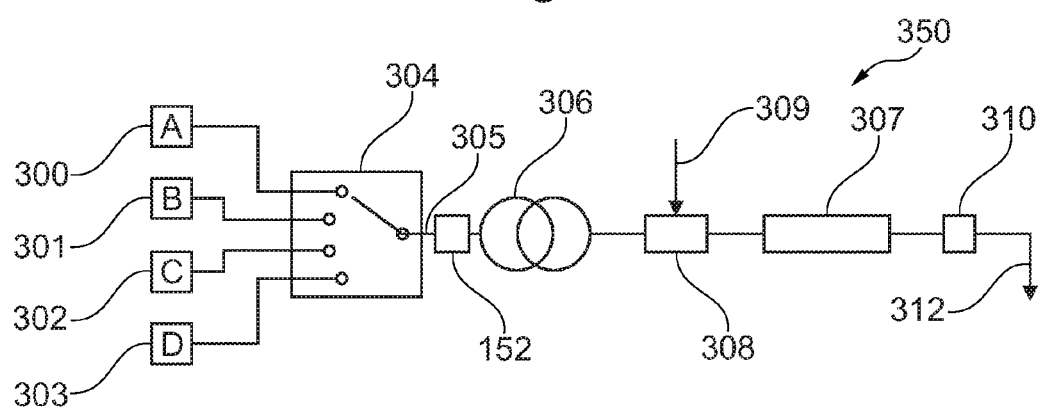
FIG. 3 shows a chromatographic sample separation system according to an exemplary embodiment of the invention.

The fluid supply system 150 shown in FIG. 1 may for example be used for supplying a flow of composite solvent to a separation device adapted for separating components of a sample liquid. FIG. 3 depicts the setup of such a sample separation system. The sample separation system comprises four reservoirs 300 to 303 containing four different solvents A, B, C, D, which are fluidically coupled with a proportioning valve 304. The proportioning valve 304 is responsible for switching between different solvents and for providing the respective solvents to an inlet 305 of the pumping unit 306 at the low-pressure side of the pumping unit. The different solvents are thus brought together at the low pressure side of the pumping unit 306. The pumping unit 306 is adapted to supply a flow of composite solvent to a separation device 307, which may for example be a chromatographic column. A sample injector 308 is located between the pumping unit 306 and the separation device 307. By means of the sample injector 308, a sample liquid 309 may be introduced into the separation flow path. The flow of composite solvent supplied by the pumping unit 306 drives the sample through the separation device 307. During passage through the separation device 307, the components of the sample are separated. A detection unit 310 located downstream of the separation device 307 is adapted to detect the various components of the sample as they appear at the outlet of the separation device 307.

Mixing unit 152, as has been described referring to FIG. 1, is located downstream the proportioning valve 304 and upstream the pumping unit 306.

The fluid supply system shown in FIG. 1, FIG. 2 is well-suited for being used in a liquid separation system, for example in a liquid chromatography system. It is to be noted, however, that the fluid supply system shown in FIG. 3 may be used in other fields as well.

Figure 4:
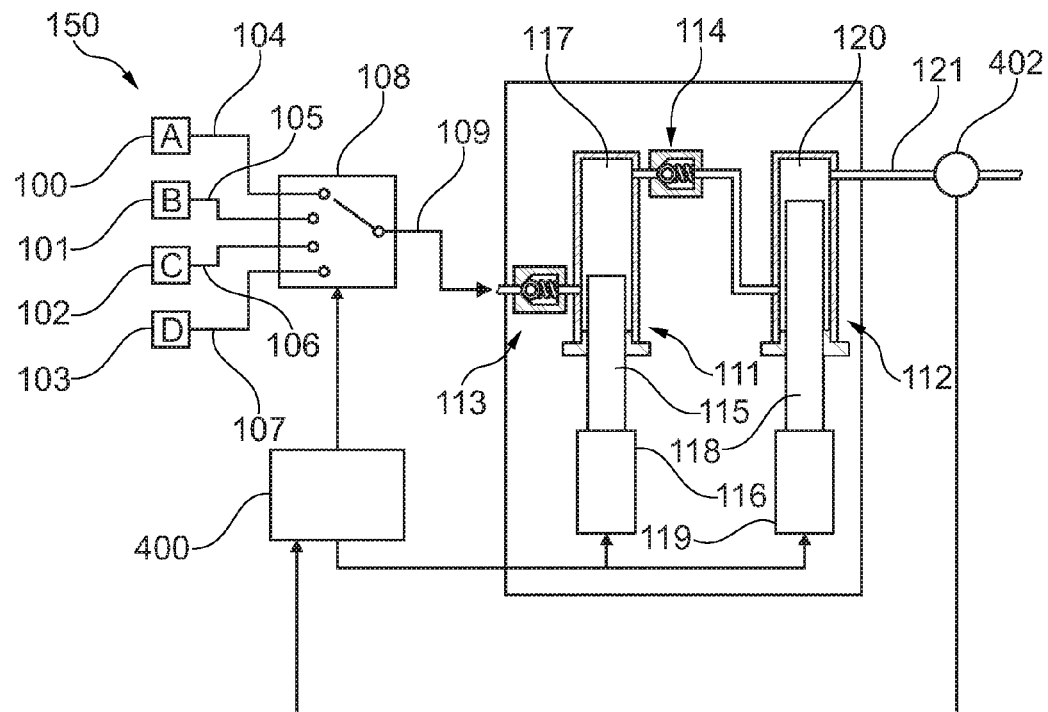
FIG. 4 illustrates a fluid supply system according to another exemplary embodiment of the invention.

FIG. 4 illustrates a fluid supply system 150 according to another exemplary embodiment of the invention.

In this embodiment, a sensor 402, for example an optical or an ultraviolet light detector, or a detector of another type such at heat conductance, flow rate, sensor, acoustic sensor, contacted or contactless conductivity sensor, refractive index transducer or sensor or alike, is arranged downstream of the pumping unit 110 and may detect the mixture and its composition flowing through the conduit 121. In case an inappropriate mixing upstream of the sensor 402 is detected by the sensor 402, it may be derived that the mixing performance has to be adapted or tuned. In case of pronounced composition deviations at the position of the sensor 402, the sensor 402 may deliver the corresponding information to a control unit 400. The control unit 400 may be a microprocessor or a central processing unit. The control unit 400 is adapted for analyzing potential mixing artifacts of the fluid in the mixture, based on the data provided by the sensor 402, resulting from density differences between the fluids and adapted for modifying operation of the fluid supply system 150 to at least partially suppress the insufficient or improper mixing. In other words, when inappropriate mixing is detected by the sensor 402, the control unit 400 changes operation of the fluid supply system 150 to improve mixing. For this purpose, it is for instance possible that the control unit 400 changes the operation of the proportioning valve 108, for instance changes the switching cycle or switching order. Additionally or alternatively, it is also possible that the operation of the pistons 116, 119 is changed for further improving the mixing homogeneity. With a feedback system, it can be detected at the position of the sensor 402 if the changes result in an improvement or a deterioration of the mixing performance. Improvements will be accepted and deteriorations will be rejected until, for instance with a trial and error algorithm, a sufficiently proper or even an optimum mixing is obtained.

It should be noted that in the embodiment of FIG. 4, it is also possible that the control unit 400, additionally or alternatively, controls a mixing unit such as the mixing unit 152 described above.

Figure 5:
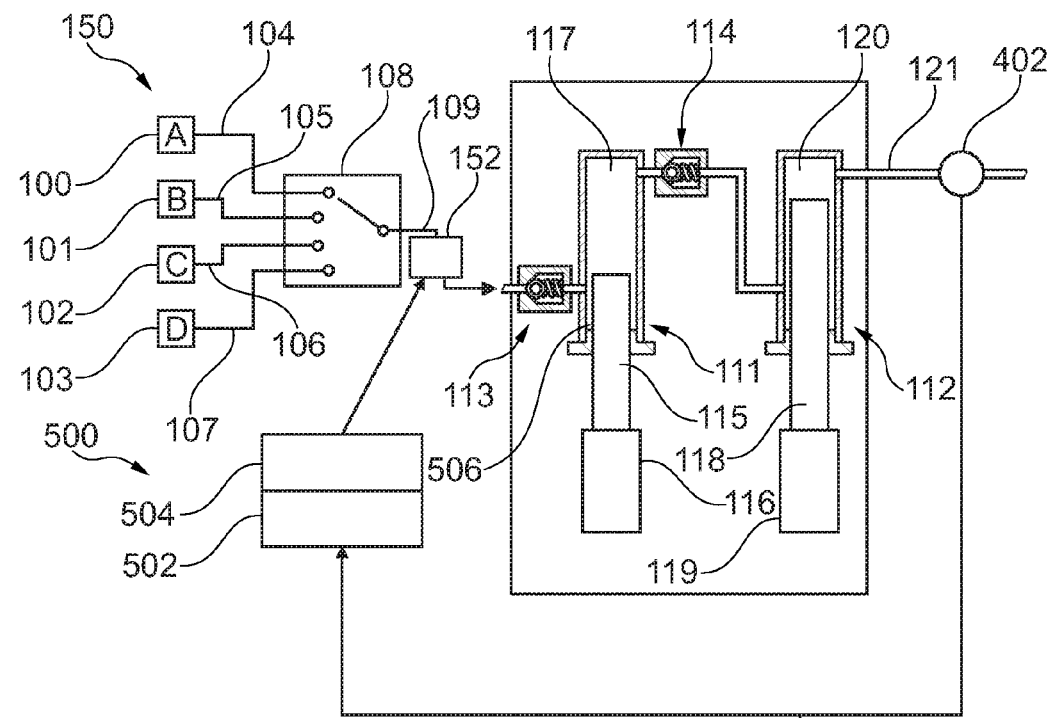
FIG. 5 illustrates a fluid supply system shown with an attached configuring device according to an exemplary embodiment of the invention.

Another embodiment of the invention is shown in FIG. 5 and shows a configuring device 500 integrated in the fluid supply system 150 shown in FIG. 1. It is however also possible that the configuring device 500 is arranged separately from the fluid supply system 150, for instance may be detachably attached to a fluid supply system 150 for calibration purposes (for instance in a factory) and can then be used for calibrating another fluid supply system 150.

In the embodiment of FIG. 5, a sensor 402 is again provided at an outlet of the pumping unit 110 to provide information regarding a potential improper mixing of the solvents coming from the containers 100 to 103. This information is supplied to a determining unit 502 of the configuring device 500 which is adapted for determining information indicative of an improper mixing of the fluids in the mixture. The determining unit 502 forwards this information to a mixing enhancing unit 504 of the configuring device 500 which is in turn adapted for changing a configuration of the fluid supply system 150 to thereby enhance mixing of the fluids in the mixture. In the shown embodiment, the mixing enhancing unit 504 can control mixing unit 152 accordingly so as to improve the mixing. It is however also possible that the output of the mixing enhancement unit 502 is used to change control of the proportioning valve 108 and/or the pumping unit 110. In still another exemplary embodiment, the mixing enhancement unit 504 suggests to a operator to manually modify the fluid supply system 150, for instance to modify a length of a connection capillary, to modify a geometry of components of the fluid supply system 150 (such as pivoting the pumping unit 110), etc.

Figure 6:
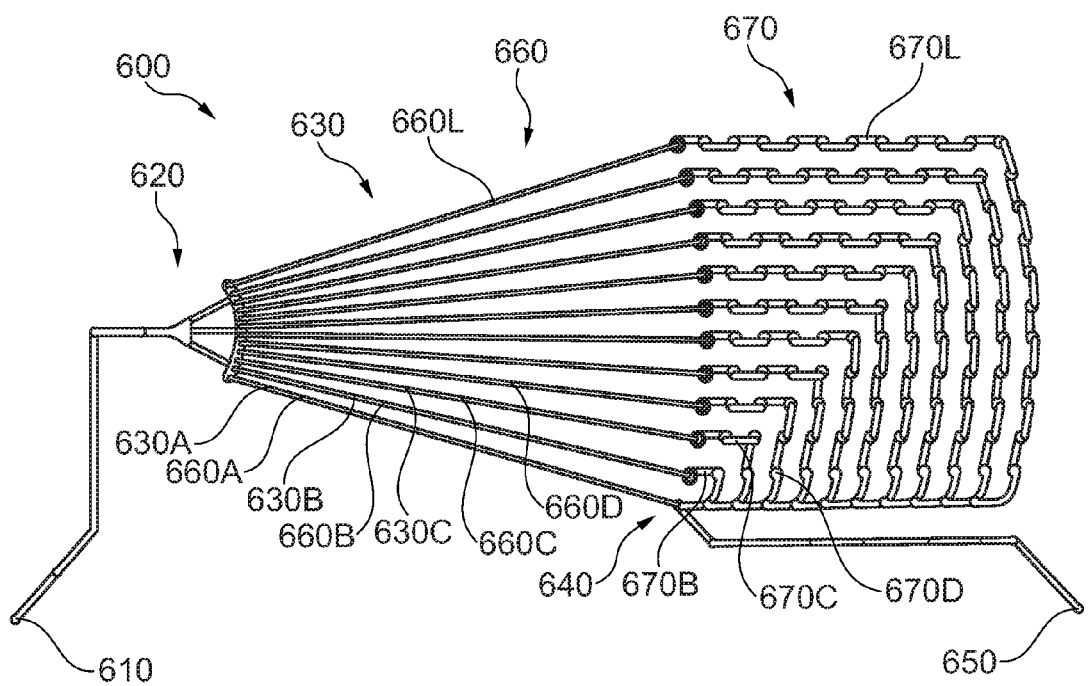
FIG. 6 illustrates a mixing unit according to an exemplary embodiment of the invention capable of splitting sections of a sequence of fluid packets into several flow paths and capable of reunifying them for mixing purposes.

FIG. 6 shows an embodiment of a mixing unit 600 according to the present invention which may be implemented in the fluid supply systems 150 as described herein as mixing unit 152. The mixing unit 600 is used for mixing a fluid differing in its property such as composition, viscosity, elution strength or temperature along a flow direction of the fluid.

In the embodiment of FIG. 6, the mixer 600 comprises an inlet 610 receiving an inlet flow of the fluid to be mixed. A flow distributor 620 receives the flow from the inlet 610 and distributes it—fluidically in parallel—into a plurality of flow channels 630. Accordingly, the flow distributor 620 provides a plurality of parallel partial flows into the plurality of (parallel) flow channels 630.

The flow distributor 620 of FIG. 6 is designed so that it substantially simultaneously distributes the fluid into the flow channels 630 and/or that a variation of the property of the fluid arrives substantially simultaneously at the first sections 660 of the flow channels 630.

In the embodiment of FIG. 6, the flow distributor 620 comprises a multi-stage configuration that provides nearly simultaneous arrival of parts of a given partial fluid volume to all the restrictor channels in combination with low distributor volume. Other embodiments are also possible in order to achieve lowest total volume of the distributor.

The plurality of flow channels 630 eventually couple to a flow combiner 640, which combines the partial flows from the plurality of flow channels 630 and provides them to an outlet flow. The outlet flow is output by an outlet 650. The flow combiner 640 is preferably designed to provide a minimum volume, as such volume of the flow combiner 640 typically contributes mainly to delay and less to mixing properties.

Each of the plurality of flow channels 630 comprises a first flow section 660, and some of the flow channels 630 further comprise a second flow section 670 coupled in series to the respective first flow section 660. In the embodiment of FIG. 6, a first flow channel 630A comprises (only) a first flow section 660A coupling directly between the flow distributor 620 and the flow combiner 640. A second flow channel 630B comprises a first flow section 660B coupling to a second flow section 670B, which then also couples into the flow combiner 640. Accordingly, a third flow channel 630C comprises a first flow section 660C coupling into a second flow section 670C, which then couples to the flow combiner 640. This continues accordingly for further flow channels. In FIG. 6, further first flow sections 660D-660L and second flow sections 670D-670L are shown, each coupling in series and eventually to the flow combiner 640.

The first flow sections 660A-660L are designed to provide a significantly larger hydraulic resistance than the respective second flow section 670B-670L, so that the total hydraulic resistance of each flow channel 630 is dominated by the hydraulic resistance of the respective first flow section 660. Further in the specific embodiment of FIG. 6, all of the first flow sections 660A-660L are designed to have substantially the same length and cross section, so that each first flow section 660 substantially has the same hydraulic resistance. Considering that the hydraulic resistance of each flow channel 630 is dominated by its respective first flow section 660, it can be assumed that each flow channel 630 can be regarded as providing substantially the same hydraulic resistance to the fluid when introduced into the flow channels 630 at the flow distributor 620. When designing the flow distributor 620 to distribute the inlet flow substantially evenly into the flow channels 630, it can be assumed that the partial flow in each flow channel is substantially equal. The distribution of the partial flows into the flow channels 630 in such embodiment is substantially independent of the viscosity of the fluid because any viscosity change arrives to the first sections 630 A-L simultaneously and the distribution ratio if the partial flows is thus maintained constant independently on the viscosity of the provided solvent.

While the hydraulic resistance of each flow channel 630 is dominated by its respective first flow section 660, each second flow section 670 has a volume delaying fluid propagation (from the respective first section 660 to the flow combiner 640) by a time required by the respective partial flow to pass the volume of the respective second flow section 670. In each flow channel 630, the volume of the second flow section 670 is designed to be significantly larger than a volume of the respective first flow section 660. In such embodiment, the propagation time of each partial flow will be mainly influenced by the volume of the respective second flow section. By providing different volumes of the respective second flow sections 670, a (desired) flow characteristic can be obtained. By having at least one flow channel 630 without second flow section, the total resulting flow characteristic of the mixer 600 can be designed to have the minimum delay as resulting from the first flow section 660 only.

Figure 7:
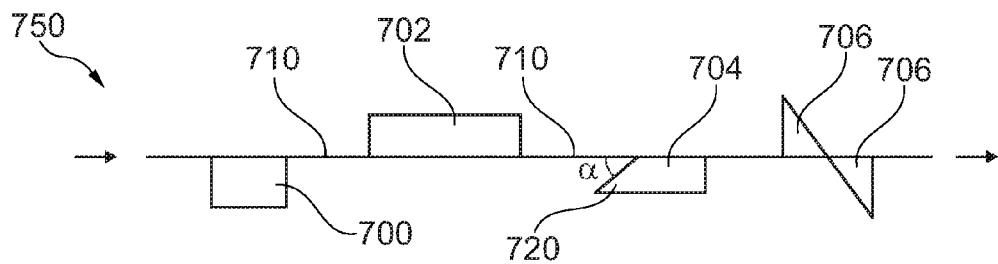
FIG. 7 schematically illustrates a mixing unit according to an exemplary embodiment of the invention having a hollow cylindrical conduit with various mixing promotion structures located along a tubular flow path.

FIG. 7 illustrates another structure implementable as the mixing unit 152 of the above embodiments of fluid supply systems 150, denoted as mixing unit 750 in FIG. 7. The mixing unit 750 comprises a tubing 710 enclosing an inner lumen (not shown) which serves as a fluid conduit for the fluid packets. Along this fluid conduit, a number of mixing structures are arranged. A first mixing structure 700 is a side volume (having a rectangular cross-section) of the tubing 710. A second mixing structure 702 is another side volume (having rectangular cross-section) of the tubing 710, however extending in the opposite direction relative to the fluid conduit 710 as compared to the first mixing structure 700. Further downstream of the second mixing structure 702 is a third mixing structure 704 with a (in the cross sectional view of FIG. 7) polygonal shaped side volume which has an acute angle α relative to the extension direction of the tubing 710 thereby forming some kind of undercut 720. Further downstream is an arrangement of two triangle shaped side volumes on opposing sites of the conduit 710 forming a fourth mixing structure 706.

With the mixing unit 750, it is possible that a fluid flowing along a direction which corresponds to the arrows shown in FIG. 7 is disturbed intentionally and in a defined way in each of the mixing structures 700, 702, 704, 706 so as to promote a mixing of subsequent fluid packets.

Figure 8:
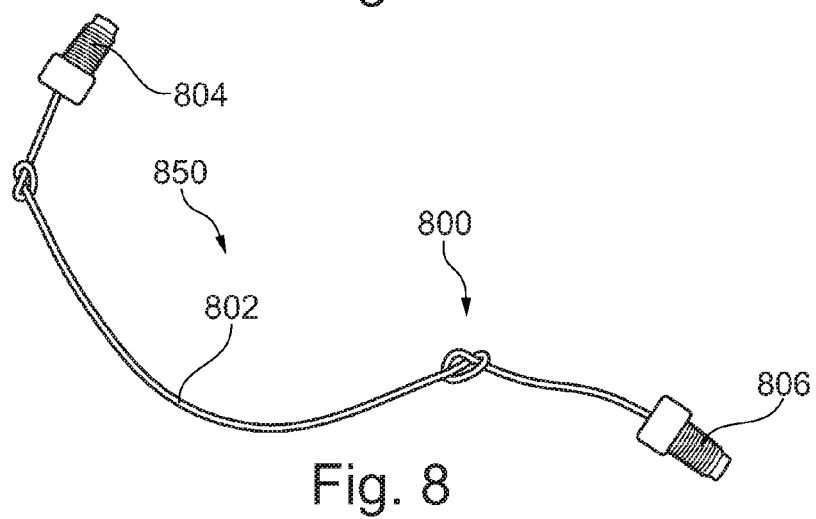
FIG. 8 shows a mixing unit according to an exemplary embodiment of the invention formed by a knotted hollow plastic tubing.

FIG. 8 illustrates another mixing unit 850 which can be used as a mixing unit 152 as shown in the above embodiments. The mixing unit 850 is formed by knotting a flexible plastic tubing 802, extending between an inlet 804 and an outlet 806, to thereby form a knotted tubing section 800. The knotted tubing section 800 is arranged between a first fitting 804 for connection to a fluidic member and a second fitting 806 for connection to another fluidic member. The knotted tubing 800 may be arranged in a flow path between the proportioning valve 108 and the pumping unit 110, i.e. as part of an intake conduit. Knotting a tubing 802 is a very simple but efficient measure of improving the mixing performance.

In the following, a conventional fluid supply system 1000 will be compared to a fluid supply system 150 according to an embodiment of the invention with regard to the fluid mixing performance. As can be taken from FIG. 9 and FIG. 10, the conventional fluid supply system 1000 shows a poor performance, whereas the fluid supply system 150 according to an embodiment of the invention provides a much better mixing performance.

Figure 9:
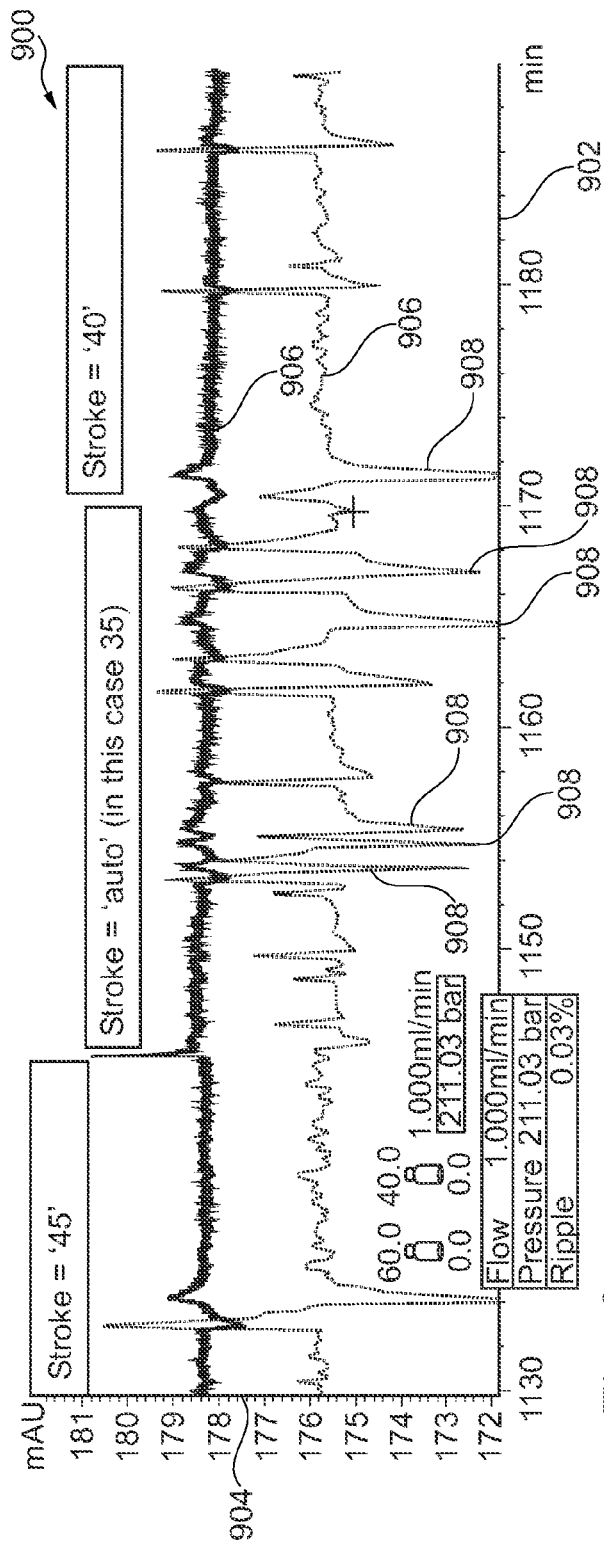
FIG. 9 shows a time dependency of a solvent composition obtained by a conventional fluid supply system showing pronounced artifacts.

FIG. 9 shows a diagram 900 having an abscissa 902 along which a measurement time is plotted in minutes. Along an ordinate 904, a measurement signal is plotted which is indicative of a concentration of a certain fluidic component of a solvent composition which is being proportionally metered and delivered by the system 1000 operating as described previously. A measurement signal 906 shown in FIG. 9 can be obtained by a sensor such as the sensor 402 shown in FIG. 4 and FIG. 5. As can be taken from FIG. 9, artifacts 908 are strongly pronounced, indicating improper mixing.

Figure 10:
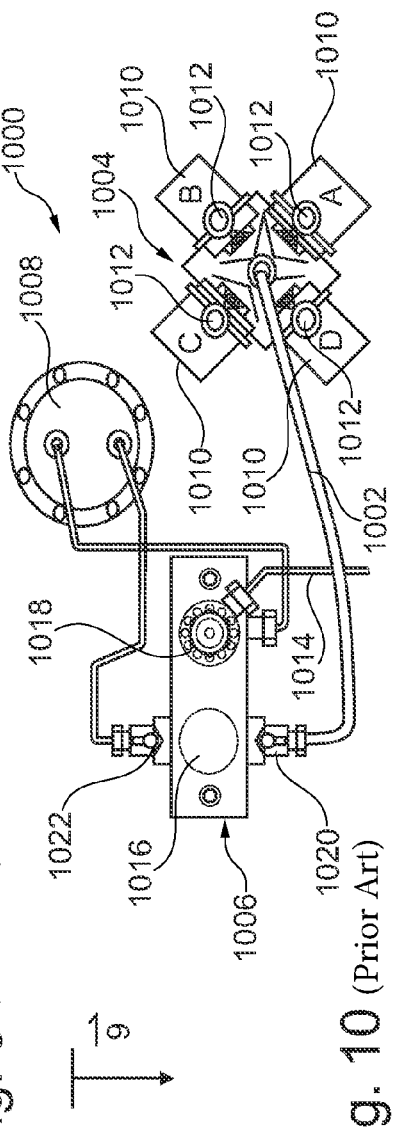
FIG. 10 shows a conventional fluid supply system relating to FIG. 9.

FIG. 10 shows a conventional fluid supply system 1000 with which the performance of FIG. 9 is obtained. A capillary 1002 fluidically couples a proportioning valve 1004 (to which four solvent supplies are connected at positions A, B, C, D) with a pump 1006. Furthermore, a damping unit 1008 may be provided (for instance an elastic chamber). The proportioning valve 1004 has four solenoids 1010 each configured for actuating a corresponding ball valve 1012 for supplying fluid packets from the bottles to the conduit 1002. Downstream of a further conduit 1014 further components of a HPLC system can be connected such as a sample injector, a separation column, etc.

The pump 1006 comprises an intake cylinder 1016 as well as a second cylinder 1018 conveying fluid into the system. A passive inlet valve 1020 is shown as well as an outlet valve 1022. For instance, the conduit 1002 sagging under the influence of the gravitational force g may cause sedimentation of high density components of the solvent composition in its lowest part as well as floating of the lighter components towards inlet valve 1020 or their backward movement back to the proportioning valve 1004.

Figure 11:
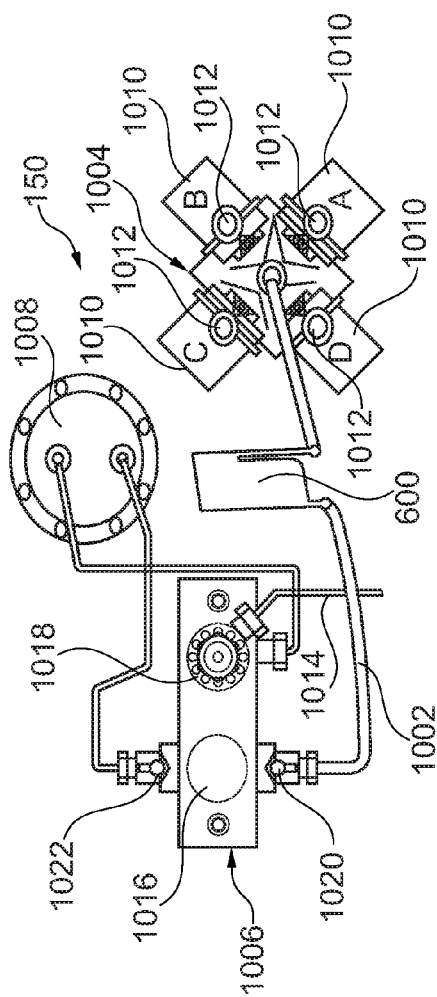
FIG. 11 shows a fluid supply system according to an exemplary embodiment of the invention.
Figure 12:
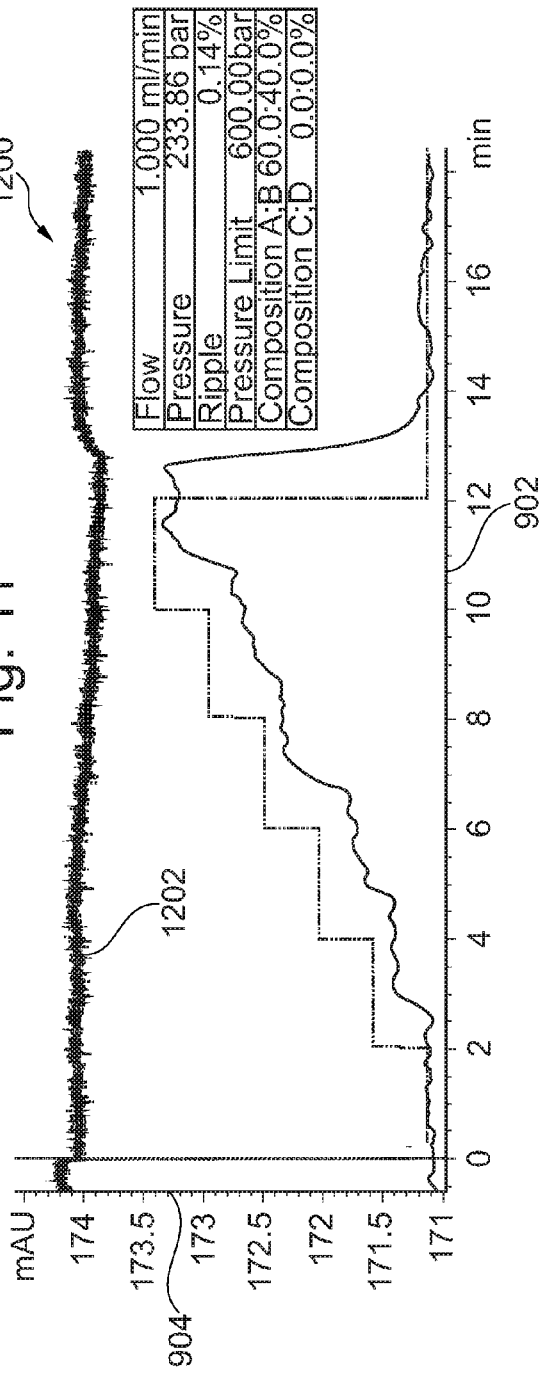
FIG. 12 shows a time dependency of a flow composition obtained with the fluid supply system of FIG. 11 and being basically free of artifacts.

FIG. 11 shows a fluid supply system 150 according to an exemplary embodiment which has, in addition to the fluid supply system 1000 in FIG. 10, a mixing unit 600. By the proper mixing in conduit 1002 between the proportioning valve 1004 and the pump 1006, the artifacts 908 can be substantially suppressed or even eliminated, as shown in the diagram 1200 of FIG. 12. This can be taken from a curve 1202 which is essentially ripple-free.

Figure 13:
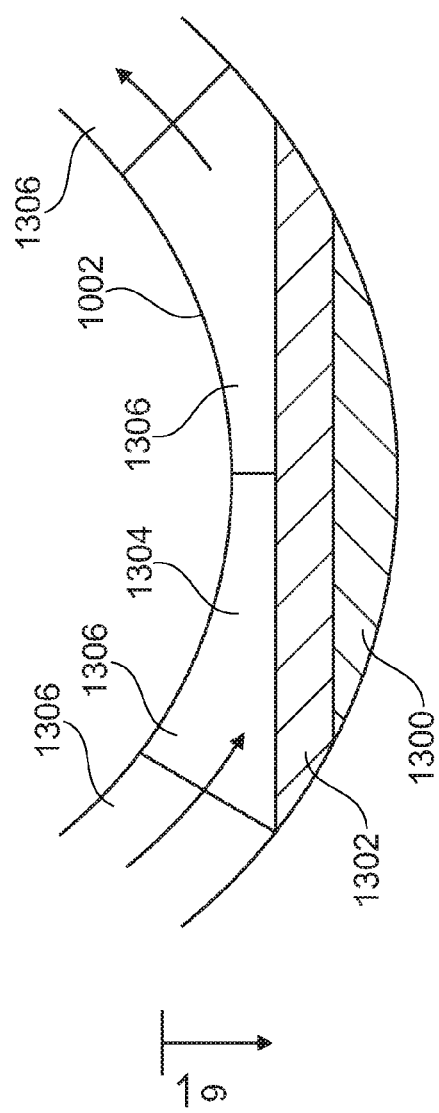
FIG. 13 illustrates sedimentation effects in a U-like sagging tube.

FIG. 13 shows sagging tube 1002 through which the solvent composition is conducted. Compare arrows in FIG. 13. FIG. 13 illustrates that a first solvent composition 1300 such as H2O which has a relatively high density can sediment at a sagging section of the tube 1002. Another fluid with a lower density as compared to water sediments above the water 1300 and is indicated with reference numeral 1302. Very low density fluid 1304 flows above the higher density fluids 1302, 1300. Therefore, fluids 1300, 1302 may remain unintentionally and undesirably long at the sagging portion of tube 1002 and may therefore become historic fluids which may deteriorate the chromatographic separation performance of the system as they become sporadically disturbed and uncontrolled admixed to an actual flow. Further shown in FIG. 13 are the sequentially supplied fluid packets 1306 of different solvents or different solvent compositions. By integrating the mixing unit 600 in the embodiment of FIG. 11, the described sedimentation or layering effects can be suppressed or even eliminated.

Figure 14:
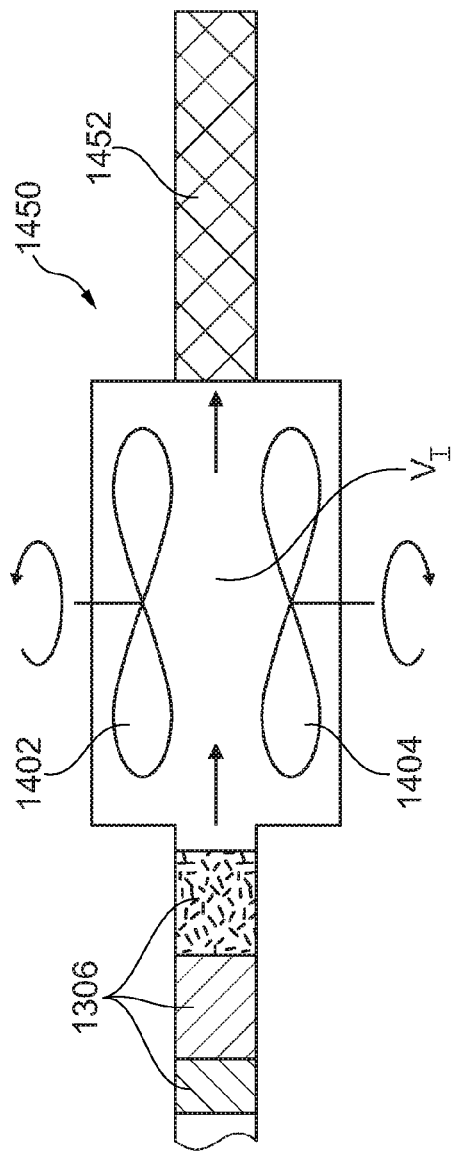
FIG. 14 illustrates a mixing unit having a very small internal fluid accommodation volume according to an exemplary embodiment of the invention.

FIG. 14 shows a mixing unit 1450 implementable according to another embodiment of the invention and having a very low internal volume $V_I$ of 50 µl. A first rotating element 1402 and a second rotating element 1404 are arranged in this chamber and may rotate for adding turbulence to fluids contained therein. Hence, fluid packets 1306 being pumped through the system will be mixed within the pumping chamber. For example, when ten components of 5 µl each are mixed, the 50 µl internal volume $V_I$ of the mixing unit 1450 is filled completely.

It should be noted that the term "comprising" does not exclude other elements or features and the term "a" or "an" does not exclude a plurality. Also elements described in association with different embodiments may be combined. It should also be noted that reference signs in the claims shall not be construed as limiting the scope of the claims.

The invention claimed is:

1. A fluid supply system adapted for metering two or more fluids in defined proportions and for supplying a resultant mixture, the fluid supply system comprising:
   a plurality of solvent supply lines, each fluidically connected with a fluid source providing a respective fluid;
   a pumping unit comprising a reciprocating element adapted for intaking fluid supplied at an inlet of the pumping unit and for supplying the pressurized fluid at an outlet of the pumping unit, wherein the pumping unit is adapted for taking in fluids in defined proportions from selected solvent supply lines and for supplying a pressurized mixture of the fluids at its outlet;
   a proportioning valve interposed between the solvent supply lines and the inlet of the pumping unit, the proportioning valve adapted for modulating solvent composition by sequentially coupling selected ones of the solvent supply lines with the inlet of the pumping unit in the course of the fluid intake phase of the pumping unit;
   a longitudinal mixing unit adapted for mixing longitudinally subsequent sections of the fluids so as to modify their succession in flow direction, wherein the longitudinal mixing unit is located downstream of the proportioning valve and upstream of the pumping unit.

2. A fluid supply system adapted for metering two or more fluids in controlled proportions and for supplying a resultant mixture, the fluid supply system comprising:
   a plurality of solvent supply lines, each fluidically connected with a fluid source providing a respective fluid;
   a pumping unit comprising a reciprocating element adapted for intaking fluid supplied at an inlet of the pumping unit and for supplying the pressurized fluid at an outlet of the pumping unit, wherein the pumping unit is adapted for taking in fluids in defined proportions from selected solvent supply lines and for supplying a pressurized mixture of the fluids at its outlet;
   a proportioning valve interposed between the solvent supply lines and the inlet of the pumping unit, the proportioning valve adapted for modulating solvent composition by sequentially coupling selected ones of the solvent supply lines with the inlet of the pumping unit in the course of the fluid intake phase of the pumping unit;
   a mixing unit adapted for mixing subsequent sections of the fluids differing in at least one of chemical composition, specific gravity, or viscosity and wherein the mixing unit has an interior fluid accommodation volume of not more than the number of solvent supply lines multiplied by a volume of one fluid section provided by the proportioning valve.

3. A fluid supply system adapted for metering two or more fluids in controlled proportions and for supplying a resultant mixture, the fluid supply system comprising:
   a plurality of solvent supply lines, each fluidically connected with a fluid source providing a respective fluid;
   a pumping unit comprising a reciprocating element adapted for intaking fluid supplied at an inlet of the pumping unit and for supplying the pressurized fluid at an outlet of the pumping unit, wherein the pumping unit is adapted for taking in fluids in defined proportions from selected solvent supply lines and for supplying a pressurized mixture of the fluids at its outlet;
   a proportioning valve interposed between the solvent supply lines and the inlet of the pumping unit, the proportioning valve adapted for modulating solvent composition by sequentially coupling selected ones of the solvent supply lines with the inlet of the pumping unit;
   a mixing unit adapted for splitting the fluids supplied at an outlet of the proportioning valve or at one or a plurality of points downstream from the outlet of the proportioning valve into a plurality of fluid paths with different internal fluid flow delay characteristics and adapted for combining the fluid paths at one or a plurality of rejoining points to thereby mix the fluids in a longitudinal fashion, wherein the mixing unit is located downstream of the proportioning valve and upstream of the pumping unit.

4. The fluid supply system of claim 3, wherein the different internal fluid flow delay characteristics are provided by different internal fluid path volumes.

5. The fluid supply system of claim 3, wherein the different internal fluid flow delay characteristics are provided by different internal fluid path flow resistances.

6. The fluid supply system of claim 2, wherein the mixing unit is located downstream of the proportioning valve and upstream of the pumping unit.

7. The fluid supply system of claim 1, wherein the mixing unit is adapted for at least partially equilibrating density fluctuations across subsequent sections of the fluids.

8. The fluid supply system of claim 1, wherein a flow path downstream of the outlet of the proportioning valve is configured to prevent variation of the distribution of the fluids caused by differences in their specific gravity.

9. The fluid supply system of claim 1, wherein a flow path downstream of the outlet of the proportioning valve is configured to prevent variation of the distribution of the fluids within subsequent sections of the fluids caused by differences in their specific gravity, whereas the mixing unit is adapted for at least partially equilibrating density fluctuations in subsequent sections of the fluids.

10. The fluid supply system of claim 1, wherein the mixing unit has an interior fluid accommodation volume of not more than 100 µl.

11. The fluid supply system of claim 1, wherein the mixing unit comprises a knotted tubing.

12. The fluid supply system of claim 1, wherein the mixing unit comprises a tubing having an inner lumen, the inner lumen comprising one or more mixing structures each providing a respective contribution to a flow resistance of the fluids in the lumen.

13. The fluid supply system of claim 12, wherein the one or more mixing structures are selected from the group consisting of: a comb structure, a vein structure, a multi-lumen tubing, a foam insert, one or more nozzles, a vortex, one or more pillars, a side volume having a rectangular cross-section, a plurality of side volumes having a rectangular cross-section with different volume values, a plurality of side volumes extending from the lumen along different directions, a side volume having a polygonal cross-section with an angle differing from a right angle, a zig-zag portion of the lumen; and a combination of two or more of the foregoing.

14. The fluid supply system of claim 1, wherein the mixing unit comprises:
    an inlet configured for receiving the fluids as an inlet flow, an outlet configured for providing the mixed fluids an outlet flow, and a plurality of flow channels coupled between the inlet and the outlet,
    a flow distributor for distributing the inlet flow into the plurality of flow channels so that each flow channel receives a partial flow from the inlet flow, and
    a flow combiner for combining the partial flows from the plurality of flow channels to the outlet flow, wherein each flow channel comprises a first flow section having a hydraulic resistance substantially representing a hydraulic resistance of the flow channel, one or more of the flow channels each comprise a second flow section coupled in series with the first flow section of the respective flow channel, each second flow section comprises a volume that is flown through by the fluid and delays fluid propagation from the first flow section to the flow combiner by a time required by the respective partial flow to pass the volume of the respective second flow section, and the distribution of the partial flows into the flow channels is substantially independent of the viscosity of the fluid.

15. The fluid supply system of claim 1, wherein the mixing unit comprises:
    an inlet configured for receiving the fluids as an inlet flow, an outlet configured for providing the mixed fluids as an outlet flow, and a plurality of flow channels coupled between the inlet and the outlet,
    a flow distributor for distributing the inlet flow into the plurality of flow channels so that each flow channel receives a partial flow from the inlet flow, and
    a flow combiner for combining the partial flows from the plurality of flow channels to the outlet flow, wherein each flow path comprises a flow direction change forcing the fluid to flow at varying angles with respect to a direction of gravitational in the subsequent subsections of the flow path.

\* \* \* \* \*